US009642993B2

(12) United States Patent
McNamara et al.

(10) Patent No.: US 9,642,993 B2
(45) Date of Patent: May 9, 2017

(54) METHODS AND DEVICES FOR INTRA-ATRIAL SHUNTS HAVING SELECTABLE FLOW RATES

(71) Applicant: Corvia Medical, Inc., Tewksbury, MA (US)

(72) Inventors: Edward McNamara, Chelmsford, MA (US); Michael W. Sutherland, Pelham, NH (US); Matthew J. Finch, Medford, MA (US); Stephen J. Forcucci, Winchester, MA (US); John Mitzel, Chester, NH (US)

(73) Assignee: Corvia Medical, Inc., Tewksbury, MA (US)

( * ) Notice: Subject to any disclaimer, the term of this patent is extended or adjusted under 35 U.S.C. 154(b) by 269 days.

(21) Appl. No.: 13/726,472

(22) Filed: Dec. 24, 2012

(65) Prior Publication Data
US 2013/0184634 A1   Jul. 18, 2013
US 2016/0184561 A9   Jun. 30, 2016

Related U.S. Application Data

(60) Provisional application No. 61/579,426, filed on Dec. 22, 2011, provisional application No. 61/659,520, filed on Jun. 14, 2012.

(51) Int. Cl.
*A61M 27/00* (2006.01)
*A61F 2/24* (2006.01)
*A61B 17/00* (2006.01)

(52) U.S. Cl.
CPC ............. *A61M 27/002* (2013.01); *A61F 2/24* (2013.01); *A61F 2/2418* (2013.01);
(Continued)

(58) Field of Classification Search
CPC ........ A61F 2/24; A61F 2/2478; A61F 2/2487; A61F 2/2493; A61F 2002/249;
(Continued)

(56) References Cited

U.S. PATENT DOCUMENTS 3,874,388 A   4/1975  King et al.
4,018,228 A   4/1977  Goosen
(Continued)

FOREIGN PATENT DOCUMENTS

AU   2007317191 A1   5/2008
CN      1218379 A    6/1999
(Continued)

OTHER PUBLICATIONS

Celermajer et al.; U.S. Appl. No. 14/498,903 entitled "Apparatus and methods to create and maintain an intra-atrial pressure relief opening," filed Sep. 26, 2014.
(Continued)

*Primary Examiner* — Jacqueline Stephens
*Assistant Examiner* — Benjamin Klein
(74) *Attorney, Agent, or Firm* — Shay Glenn LLP

(57) ABSTRACT

Devices and methods for treating heart disease by normalizing elevated blood pressure in the left and right atria of a heart of a mammal are disclosed. The devices are adapted to permit fluid flow across the membrane in which the device is implanted at first rate, and at a second rate, wherein a difference between the first rate and the second rate is not solely dependent upon variations in blood pressure differential across the membrane due to the heart's pumping cycle.

35 Claims, 17 Drawing Sheets

(52) U.S. Cl.
CPC .. *A61F 2/2493* (2013.01); *A61B 2017/00247* (2013.01); *A61B 2017/00575* (2013.01); *A61B 2017/00584* (2013.01); *A61B 2017/00592* (2013.01); *A61B 2017/00606* (2013.01); *A61B 2017/00623* (2013.01); *A61F 2/2412* (2013.01)

(58) Field of Classification Search
CPC ....... A61F 2210/0004; A61M 5/16813; A61M 27/00–27/002
USPC ...................................................... 604/8–10
See application file for complete search history.

(56) References Cited

U.S. PATENT DOCUMENTS

| | | | |
|---|---|---|---|
| 4,373,216 A | 2/1983 | Klawitter | |
| 4,491,986 A | 1/1985 | Gabbay | |
| 4,705,507 A | 11/1987 | Boyles | |
| 5,100,423 A | 3/1992 | Fearnot | |
| 5,108,420 A | 4/1992 | Marks | |
| 5,171,233 A | 12/1992 | Amplatz et al. | |
| 5,284,488 A | 2/1994 | Sideris | |
| 5,332,402 A | 7/1994 | Teitelbaum | |
| 5,334,217 A | 8/1994 | Das | |
| 5,413,599 A | 5/1995 | Imachi et al. | |
| 5,429,144 A | 7/1995 | Wilk | |
| 5,433,727 A | 7/1995 | Sideris | |
| 5,464,449 A | 11/1995 | Ryan et al. | |
| 5,478,353 A | 12/1995 | Yoon | |
| 5,556,386 A | 9/1996 | Todd | |
| 5,556,408 A | 9/1996 | Farhat | |
| 5,578,045 A | 11/1996 | Das | |
| 5,693,090 A | 12/1997 | Unsworth et al. | |
| 5,702,412 A | 12/1997 | Popov et al. | |
| 5,725,552 A | 3/1998 | Kotula et al. | |
| 5,824,071 A | 10/1998 | Nelson et al. | |
| 5,846,261 A | 12/1998 | Kotula et al. | |
| 5,876,436 A | 3/1999 | Vanney et al. | |
| 5,893,369 A | 4/1999 | Lemole | |
| 5,944,738 A | 8/1999 | Amplatz et al. | |
| 5,964,754 A | 10/1999 | Osypka | |
| 6,050,936 A | 4/2000 | Schweich, Jr. et al. | |
| 6,059,827 A | 5/2000 | Fenton | |
| 6,068,635 A | 5/2000 | Gianotti | |
| 6,077,281 A | 6/2000 | Das | |
| 6,120,534 A | 9/2000 | Ruiz | |
| 6,123,682 A | 9/2000 | Knudson et al. | |
| 6,123,715 A | 9/2000 | Amplatz | |
| 6,152,937 A | 11/2000 | Peterson et al. | |
| 6,156,055 A | 12/2000 | Ravenscroft | |
| 6,168,622 B1 | 1/2001 | Mazzocchi | |
| 6,190,353 B1 | 2/2001 | Makower et al. | |
| 6,193,734 B1 | 2/2001 | Bolduc et al. | |
| 6,210,338 B1 | 4/2001 | Afremov et al. | |
| 6,241,678 B1 | 6/2001 | Afremov et al. | |
| 6,258,119 B1 | 7/2001 | Hussein et al. | |
| 6,286,512 B1 | 9/2001 | Loeb et al. | |
| 6,334,864 B1 | 1/2002 | Amplatz et al. | |
| 6,350,277 B1 | 2/2002 | Kocur | |
| 6,355,052 B1 | 3/2002 | Neuss et al. | |
| 6,355,056 B1 | 3/2002 | Pinheiro | |
| 6,357,735 B2 | 3/2002 | Haverinen | |
| 6,383,195 B1 | 5/2002 | Richard | |
| 6,395,017 B1 | 5/2002 | Dwyer et al. | |
| 6,402,777 B1 | 6/2002 | Globerman et al. | |
| 6,409,716 B1 | 6/2002 | Sahatjian et al. | |
| 6,440,152 B1 | 8/2002 | Gainor et al. | |
| 6,454,795 B1 | 9/2002 | Chuter | |
| 6,458,153 B1 | 10/2002 | Bailey et al. | |
| 6,468,301 B1 | 10/2002 | Amplatz et al. | |
| 6,468,303 B1 | 10/2002 | Amplatz et al. | |
| 6,527,746 B1 | 3/2003 | Oslund et al. | |
| 6,572,652 B2 | 6/2003 | Shaknovich | |
| 6,579,311 B1 | 6/2003 | Makower | |
| 6,599,308 B2 | 7/2003 | Amplatz | |
| 6,626,936 B2 | 9/2003 | Stinson | |
| 6,638,257 B2 | 10/2003 | Amplatz | |
| 6,641,610 B2 | 11/2003 | Wolf et al. | |
| 6,645,143 B2 | 11/2003 | VanTassel et al. | |
| 6,666,885 B2 | 12/2003 | Moe | |
| 6,712,836 B1 | 3/2004 | Berg et al. | |
| 6,719,768 B1 | 4/2004 | Cole et al. | |
| 6,837,901 B2 | 1/2005 | Rabkin et al. | |
| 6,866,679 B2 | 3/2005 | Kusleika | |
| 6,911,037 B2 | 6/2005 | Gainor et al. | |
| 6,913,614 B2 | 7/2005 | Marino et al. | |
| 6,932,837 B2 | 8/2005 | Amplatz et al. | |
| 6,936,058 B2 | 8/2005 | Forde et al. | |
| 6,979,343 B2 | 12/2005 | Russo et al. | |
| 7,001,409 B2 | 2/2006 | Amplatz | |
| 7,033,372 B1 | 4/2006 | Cahalan | |
| 7,037,329 B2 | 5/2006 | Martin | |
| 7,044,134 B2 | 5/2006 | Khairkhahan et al. | |
| 7,097,653 B2 | 8/2006 | Freudenthal et al. | |
| 7,105,024 B2 | 9/2006 | Richelsoph | |
| 7,159,593 B2 | 1/2007 | McCarthy et al. | |
| 7,226,466 B2 | 6/2007 | Opolski | |
| 7,317,951 B2 | 1/2008 | Schneider et al. | |
| 7,338,514 B2 | 3/2008 | Wahr et al. | |
| 7,350,995 B1 | 4/2008 | Rhodes | |
| 7,419,498 B2 | 9/2008 | Opolski et al. | |
| 7,445,630 B2 | 11/2008 | Lashinski et al. | |
| 7,473,266 B2 | 1/2009 | Glaser | |
| 7,485,141 B2 | 2/2009 | Majercak et al. | |
| 7,524,330 B2 | 4/2009 | Berreklouw | |
| 7,530,995 B2 | 5/2009 | Quijano et al. | |
| 7,611,534 B2 | 11/2009 | Kapadia et al. | |
| 7,625,392 B2 | 12/2009 | Coleman et al. | |
| 7,658,747 B2 | 2/2010 | Forde et al. | |
| 7,678,123 B2 | 3/2010 | Chanduszko | |
| 7,691,144 B2 | 4/2010 | Chang et al. | |
| 7,699,297 B2 | 4/2010 | Cicenas et al. | |
| 7,704,268 B2 | 4/2010 | Chanduszko | |
| 7,722,629 B2 | 5/2010 | Chambers | |
| 7,766,966 B2 | 8/2010 | Richelsoph | |
| 7,819,890 B2 | 10/2010 | Russo et al. | |
| 7,842,026 B2 | 11/2010 | Cahill et al. | |
| 7,871,419 B2 | 1/2011 | Devellian et al. | |
| 7,905,901 B2 | 3/2011 | Corcoran et al. | |
| 7,927,370 B2 | 4/2011 | Webler et al. | |
| 7,967,769 B2 | 6/2011 | Faul et al. | |
| 7,976,564 B2 | 7/2011 | Blaeser et al. | |
| 8,010,186 B1 | 8/2011 | Ryu | |
| 8,021,359 B2 | 9/2011 | Auth et al. | |
| 8,034,061 B2 | 10/2011 | Amplatz et al. | |
| 8,043,360 B2 | 10/2011 | McNamara et al. | |
| 8,048,147 B2 | 11/2011 | Adams | |
| 8,052,750 B2 | 11/2011 | Tuval et al. | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,252,042 B2 | 8/2012 | McNamara et al. | |
| 8,303,623 B2 | 11/2012 | Melzer et al. | |
| 8,313,505 B2 | 11/2012 | Amplatz et al. | |
| 8,366,088 B2 | 2/2013 | Allen et al. | |
| 8,398,670 B2 | 3/2013 | Amplatz et al. | |
| 8,460,372 B2 | 6/2013 | McNamara et al. | |
| 8,777,974 B2 | 7/2014 | Amplatz et al. | |
| 8,864,822 B2 | 10/2014 | Spence et al. | |
| 8,979,923 B2 | 3/2015 | Spence et al. | |
| 2001/0027287 A1 | 10/2001 | Shmulewitz et al. | |
| 2001/0029368 A1 | 10/2001 | Berube | |
| 2001/0053932 A1 | 12/2001 | Phelps et al. | |
| 2002/0029061 A1 | 3/2002 | Amplatz et al. | |
| 2002/0062135 A1 | 5/2002 | Mazzocchi et al. | |
| 2002/0072765 A1 | 6/2002 | Mazzocchi et al. | |
| 2002/0077698 A1 | 6/2002 | Peredo | |
| 2002/0082525 A1 | 6/2002 | Oslund et al. | |
| 2002/0082613 A1 | 6/2002 | Hathaway et al. | |
| 2002/0095172 A1 | 7/2002 | Mazzocchi et al. | |
| 2002/0095173 A1 | 7/2002 | Mazzocchi et al. | |
| 2002/0120277 A1 | 8/2002 | Hauschild et al. | |
| 2002/0143289 A1 | 10/2002 | Ellis et al. | |

(56) References Cited

U.S. PATENT DOCUMENTS

| | | |
|---|---|---|
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2002/0198563 A1 | 12/2002 | Gainor et al. |
| 2003/0093072 A1 | 5/2003 | Friedman |
| 2003/0125798 A1 | 7/2003 | Martin |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | Mccarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamoto et al. |
| 2005/0049697 A1 | 3/2005 | Sievers |
| 2005/0065507 A1 | 3/2005 | Hartley et al. |
| 2005/0065548 A1 | 3/2005 | Marino et al. |
| 2005/0065589 A1 | 3/2005 | Schneider et al. |
| 2005/0070934 A1 | 3/2005 | Tanaka et al. |
| 2005/0075655 A1 | 4/2005 | Bumbalough et al. |
| 2005/0080400 A1 | 4/2005 | Corcoran et al. |
| 2005/0080430 A1 | 4/2005 | Wright et al. |
| 2005/0096735 A1 | 5/2005 | Hojeibane et al. |
| 2005/0113868 A1 | 5/2005 | Devellian et al. |
| 2005/0131503 A1 | 6/2005 | Solem |
| 2005/0137609 A1 | 6/2005 | Guiraudon |
| 2005/0137686 A1 | 6/2005 | Salahieh et al. |
| 2005/0148925 A1 | 7/2005 | Rottenberg et al. |
| 2005/0165344 A1 | 7/2005 | Dobak, III |
| 2005/0187616 A1 | 8/2005 | Realyvasquez |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267523 A1 | 12/2005 | Devellian et al. |
| 2005/0267524 A1 | 12/2005 | Chanduszko |
| 2005/0273075 A1 | 12/2005 | Krulevitch et al. |
| 2005/0273124 A1 | 12/2005 | Chanduszko |
| 2005/0288722 A1 | 12/2005 | Eigler et al. |
| 2006/0004323 A1 | 1/2006 | Chang et al. |
| 2006/0004434 A1 | 1/2006 | Forde et al. |
| 2006/0009715 A1 | 1/2006 | Khairkhahan et al. |
| 2006/0009800 A1 | 1/2006 | Christianson et al. |
| 2006/0009832 A1 | 1/2006 | Fisher |
| 2006/0041183 A1 | 2/2006 | Massen et al. |
| 2006/0085060 A1 | 4/2006 | Campbell |
| 2006/0095066 A1 | 5/2006 | Chang et al. |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0210605 A1 | 9/2006 | Chang et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0005127 A1 | 1/2007 | Boekstegers et al. |
| 2007/0016250 A1 | 1/2007 | Blaeser et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0168019 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039881 A1 | 2/2008 | Greenberg |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0109069 A1 | 5/2008 | Coleman et al. |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0221582 A1 | 9/2008 | Gia et al. |
| 2008/0228264 A1 | 9/2008 | Li et al. |
| 2008/0249397 A1 | 10/2008 | Kapadia |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018562 A1 | 1/2009 | Amplatz et al. |
| 2009/0018570 A1 | 1/2009 | Righini et al. |
| 2009/0025820 A1 | 1/2009 | Adams |
| 2009/0030495 A1 | 1/2009 | Koch |
| 2009/0054805 A1 | 2/2009 | Boyle |
| 2009/0054984 A1 | 2/2009 | Shortkroff et al. |
| 2009/0062841 A1 | 3/2009 | Amplatz et al. |
| 2009/0076541 A1 | 3/2009 | Chin et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0112251 A1 | 4/2009 | Qian et al. |
| 2009/0131978 A1 | 5/2009 | Gainor et al. |
| 2009/0171386 A1 | 7/2009 | Amplatz et al. |
| 2009/0177269 A1 | 7/2009 | Kalmann et al. |
| 2009/0187214 A1 | 7/2009 | Amplatz et al. |
| 2009/0209855 A1 | 8/2009 | Drilling et al. |
| 2009/0209999 A1 | 8/2009 | Afremov |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul, Jr. et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030259 A1 | 2/2010 | Pavcnik et al. |
| 2010/0030321 A1 | 2/2010 | Mach |
| 2010/0049307 A1 | 2/2010 | Ren |

(56) References Cited

U.S. PATENT DOCUMENTS

| | | |
|---|---|---|
| 2010/0051886 A1 | 3/2010 | Cooke et al. |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0114140 A1 | 5/2010 | Chanduszko |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249490 A1 | 9/2010 | Farnan |
| 2010/0249491 A1 | 9/2010 | Farnan et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0268316 A1 | 10/2010 | Brenneman et al. |
| 2010/0274351 A1 | 10/2010 | Rolando et al. |
| 2010/0298755 A1 | 11/2010 | McNamara et al. |
| 2010/0305685 A1 | 12/2010 | Millwee et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0087261 A1 | 4/2011 | Wittkampf et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0184439 A1 | 7/2011 | Anderson et al. |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg |
| 2011/0257723 A1 | 10/2011 | Mcnamara |
| 2011/0270239 A1 | 11/2011 | Werneth |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2011/0319806 A1* | 12/2011 | Wardle ............... A61F 9/00781 604/8 |
| 2011/0319989 A1 | 12/2011 | Lane et al. |
| 2012/0022427 A1 | 1/2012 | Kapadia |
| 2012/0053686 A1 | 3/2012 | Mcnamara et al. |
| 2012/0130301 A1 | 5/2012 | Mcnamara et al. |
| 2012/0165928 A1 | 6/2012 | Nitzan et al. |
| 2012/0259263 A1 | 10/2012 | Celermajer et al. |
| 2012/0265296 A1 | 10/2012 | Mcnamara et al. |
| 2012/0289882 A1 | 11/2012 | Mcnamara et al. |
| 2012/0290062 A1 | 11/2012 | Mcnamara et al. |
| 2012/0290077 A1 | 11/2012 | Aklog et al. |
| 2013/0030521 A1* | 1/2013 | Nitzan ............... A61B 17/0057 623/2.13 |
| 2013/0041359 A1 | 2/2013 | Asselin et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0204175 A1 | 8/2013 | Sugimoto |
| 2013/0231737 A1 | 9/2013 | McNamara et al. |
| 2013/0267885 A1 | 10/2013 | Celermajer et al. |
| 2013/0281988 A1 | 10/2013 | Magnin et al. |
| 2014/0012181 A1 | 1/2014 | Sugimoto et al. |
| 2014/0012368 A1 | 1/2014 | Sugimoto et al. |
| 2014/0194971 A1 | 7/2014 | McNamara |
| 2014/0257167 A1 | 9/2014 | Celermajer et al. |
| 2014/0277054 A1 | 9/2014 | McNamara et al. |
| 2015/0039084 A1* | 2/2015 | Levi ............... A61B 17/0057 623/2.38 |
| 2015/0119796 A1 | 4/2015 | Finch |
| 2016/0022423 A1 | 1/2016 | McNamara et al. |
| 2016/0022970 A1 | 1/2016 | Forcucci et al. |
| 2016/0051800 A1 | 2/2016 | Vassiliades et al. |
| 2016/0166381 A1 | 6/2016 | Sugimoto et al. |

FOREIGN PATENT DOCUMENTS

| | | |
|---|---|---|
| CN | 1556719 A | 12/2004 |
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| CN | 102905626 A | 1/2013 |
| CN | 102908213 A | 2/2013 |
| EP | 1264582 A2 | 2/2002 |
| EP | 1470785 A1 | 10/2004 |
| EP | 1849440 A1 | 10/2007 |
| EP | 2528646 A2 | 12/2012 |
| EP | 2537490 A1 | 12/2012 |
| JP | 58-27935 U | 6/1983 |
| JP | 2003530143 | 10/2003 |
| WO | 9527448 A1 | 10/1995 |
| WO | WO98/08456 A1 | 3/1998 |
| WO | WO98/42403 A1 | 10/1998 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | WO2007/083288 A2 | 7/2007 |
| WO | 2008055301 A1 | 5/2008 |
| WO | 2008058940 A1 | 5/2008 |
| WO | 2010111666 A1 | 9/2010 |
| WO | 2010128501 A1 | 11/2010 |
| WO | 2010129089 A2 | 11/2010 |
| WO | WO2010/129511 A2 | 11/2010 |
| WO | 2011093941 A2 | 8/2011 |
| WO | 2011094521 A2 | 8/2011 |
| WO | 2011093941 A3 | 10/2011 |
| WO | 2011093941 A4 | 12/2011 |
| WO | 2011094521 A3 | 12/2011 |
| WO | 2012071075 A1 | 5/2012 |
| WO | 2012109557 A2 | 8/2012 |
| WO | 2012109557 A3 | 1/2013 |
| WO | 2013096965 A1 | 6/2013 |

OTHER PUBLICATIONS

Ling et al.; Implantable magnetic relaxation sensors measure cumulative exposure to cardiac biomarkers; Nat Biotechnol; 29(3); pp. 273-277; Mar. 2011.

McMahon, Jim; Piezo motors and actuators: Streamlining medical device performance; Designfax; Mar. 23, 2010; 5 pgs.; retrieved from the internet on Jul. 19, 2012 (http://www.designfax.net/enews/20100323/feature-1.asp).

Physik Instrumente; Piezo for Motion Control in Medical Design and Drug Research (product information); Physik Instrumente (PI) GmbH & Co. KG; 22 pgs.; © Nov. 21, 2010.

Roven et al.; Effect of compromising right ventricular function in left ventricular failure by means of interatrial and other shunts; Am J Cardiol.; 24(2); pp. 209-219; Aug. 1969.

RPI Newswire; Implantable, wireless sensors share secrets of healing tissues; RPI Newswire; 1 pg.; Feb. 21, 2012; retrieved from the internet on Jul. 18, 2012 (http://news.rpi.edu/update.do).

Sambhi et al.; Pathologic Physiology of Lutembacher Syndrome; Am J Cardiol.; 2(6); pp. 681-686; Dec. 1958.

Trafton, Anne; Detecting whether a heart attack has occurred; MIT News; 3 pgs.; Feb. 14, 2011; retrieved from the internet Sep. 20, 2014 (http://newsoffice.mit.edu/2011/cardiac-implant-0214).

(56) References Cited

OTHER PUBLICATIONS

Webber, Ralph; Piezo Motor Based Medical Devices; Medical Design Technology; 5 pgs.; Apr. 2, 2009; retrieved from the internet on Jul. 19, 2012 (http://mdtmag.com/articles/2009/04/piezo-motor-based-medical-devices).
PCT/US12/024680, International Application Serial No. PCT/US12/024680, International Preliminary Report on Patentability and Written Opinion mailed Aug. 22, 2013, DC Devices, Inc, 7 pages.
PCT/US2011/041841, International Application Serial No. PCT/US2011/041841, International Preliminary Report on Patentability and Written Opinion mailed Jun. 6, 2013, DC Devices, Inc. et al., 8 pages.
PCT/US2012/071588, International Application Serial No. PCT/US2012/071588, International Search Report and Written Opinion mailed Apr. 19, 2013, DC Devices, Inc., 19 pages.
European Application Serial No. 10772411, European Search Opinion and Supplementary European Search Report mailed Mar. 16, 2012, 5 pages.
Ad et al., "A one way valved atrial septal patch: A new surgical technique and its clinical application", The Journal of Thoracic and Cardiovascular Surgery, vol. 111, No. 4, Apr. 1996, pp. 841-848.
Althoff et al., "Long-Term follow up of a fenestrated amplatzer atrial septal occluder in pulmonary arterial hypertension", American College of Chest Physicians 2008, Chest, vol. 133, No. 1, Jan. 2008, 5 pages.
Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp. 1224-1228.
Bailey, Steven R., "Nanotechnology in prosthetic heart valves", EuroPCR 2005, May 24-27, 2005, 31 pages.
Bolling, Steven F., "Direct Flow medical-my valve is better", Direct Flow medical Inc., Apr. 23, 2009, 21 pages.
Caselli, Joseph S., "No! valve replacement: patient prosthetic mismatch rarely occurs", Texas Heart Institute, Apr. 25, 2009, 75 pages.
Cheatham, John P., "Intervention in the critically ill neonate and infant with hypoplastic left heart syndrome and intact atrial septum", Journal of Interventional Cardiology, vol. 14, No. 3, 2001, 357-366.
Design News, "Low Power Piezo Motion", http://www.designnews.com/document.asp?doc_id=229053&dfpPParams& dfpPParams=ht_13,aid_229053&dfpLayout=article, May 14, 2010, 3 pages.
European Application Serial No. EP12180631.9, European Search Report mailed Nov. 19, 2012, 5 pages.
Gaudiani et al., "A philosophical approach to mitrel valve repair", Dallas-Leipzig International Valve Congress, Apr. 24, 2009, 28 pages.
Hijazi, Ziyad M., "Valve Implantation", Pediatric & Adult Interventional Therapies for Congenital and Valvular Heart. Disease, Jul. 22-25, 2007, 36 pages.
Larios et al., "The Use of an Artificial Foraminal Valve Prosthesis in the Closure of Interatrial and Interventricular Septal Defects", American Ccollege of Chest Physicains, Dis. Chest. 1959, vol. 36, Dec. 1959, 12 pages.
Leon, Martin B., "Transcatheter Aortic Valve Therapy: Summary Thoughts", Transcatheter Valve Therapies, Jun. 24-26, 2009, 19 pages.
Merchant et al., "Advances in Arrhythmia and Electrophysiology; Implantable Sensors for Heart Failure", Circ. Arrhythm. Electrophysiol., vol. 3, Dec. 2010, pp. 657-667.
Moses, Jeffrey W., "The Good, the Bad and the ugly of transcatheter AVR", Jul. 10, 2009, 28 pages.
O'Loughlin et al., "Insertion of a Fenestrated Amplatzer Atrial Sestosotomy Device for Severe Pulmonary Hypertension", Heart , Lung and Circulation, vol. 15, 2006, pp. 275-277.
Park et al., "Blade atrial septostomy: collaborative study", Circulation, Journal of the American Heart Association, , vol. 66, No. 2, Aug. 1982, pp. 10.
International Application Serial No. PCT/AU2007/001704, International Search Report mailed Jan. 16, 2008, 4 pages.
International Application Serial No. PCT/AU2007/01704, International Preliminary Report on Patentability mailed Aug. 22, 2008, 5 pages.
International Application Serial No. PCT/AU2007/01704, Written Opinion mailed Jan. 16, 2008, 5 pages.
International Application Serial No. PCT/US10/58110, International Preliminary Report on Patentability mailed Nov. 27, 2012, 11 pages.
International Application Serial No. PCT/US2010/026574, International Preliminary Report on Patentability mailed Nov. 10, 2011,7 pages.
International Application Serial No. PCT/US2010/026574, International Search Report and Written Opinion mailed Nov. 19, 2010,9 pages.
International Application Serial No. PCT/US2010/58110, International Search Report and Written Opinion mailed Aug. 26, 2011, 14 pages.
International Application Serial No. PCT/US2011/041841, International Search Report mailed Feb. 9, 2012, 12 pages.
International Application Serial No. PCT/US2011/22895, International Search Report & Written Opinion mailed Oct. 24, 2011, 11 pages.
International Application Serial No. PCT/US2012/024680, International Search Report and Written Opinion mailed Oct. 23, 2012, 11 pages.
Pedra et al., "Stent Implantation to Create Interatrial Communications in Patients With Complex Congenital Heart Disease", Catheterization and Cardiovascular Interventions 47, Jan. 27, 1999, pp. 310-313.
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al., "Ventriculofemoroatrial shunt: a viable alternative for the treatment of hydrocephalus", J. Neurosurg., vol. 86, Jun. 1997, pp. 1063-1066.
Sommer et al., "Transcatheter Creation of Atrial Septal Defect and Fontan Fenestration with "Butterfly" Stent Technique", Supplement to Journal of the American College of Cardiology, V. 33, No. 2, Supplement A, Feb. 1999, 3 pages.
Stone, Gregg W., "Transcatheter devices for mitrel valve repair surveying the landscape", Columbia University Medical Center, Jul. 10, 2009, 48 pages.
Stormer et al., "Comparative Study of in vitro Flow Characteristics between a Human Aortic Valve and a Designed Aortic Valve and Six Corresponding Types of Prosthetic Heart Valves", Eur. Surg. Res., vol. 8, No. 2, 1976, pp. 117-131.
Watterson et al., "Very Small Pulmonary Arteries: Central End-to-Side Shunt", Ann. Thorac. Surg., vol. 52, No. 5, Nov. 1991, pp. 1132-1137.
McNamara et al.; U.S. Appl. No. 14/612,022 entitled "Methods and devices for intra-atrial shunts having adjustable sizes," filed Feb. 2, 2015.
Finch; U.S. Appl. No. 14/645,416 entitled "Devices and methods for treating heart failure," filed Mar. 11, 2015.

\* cited by examiner

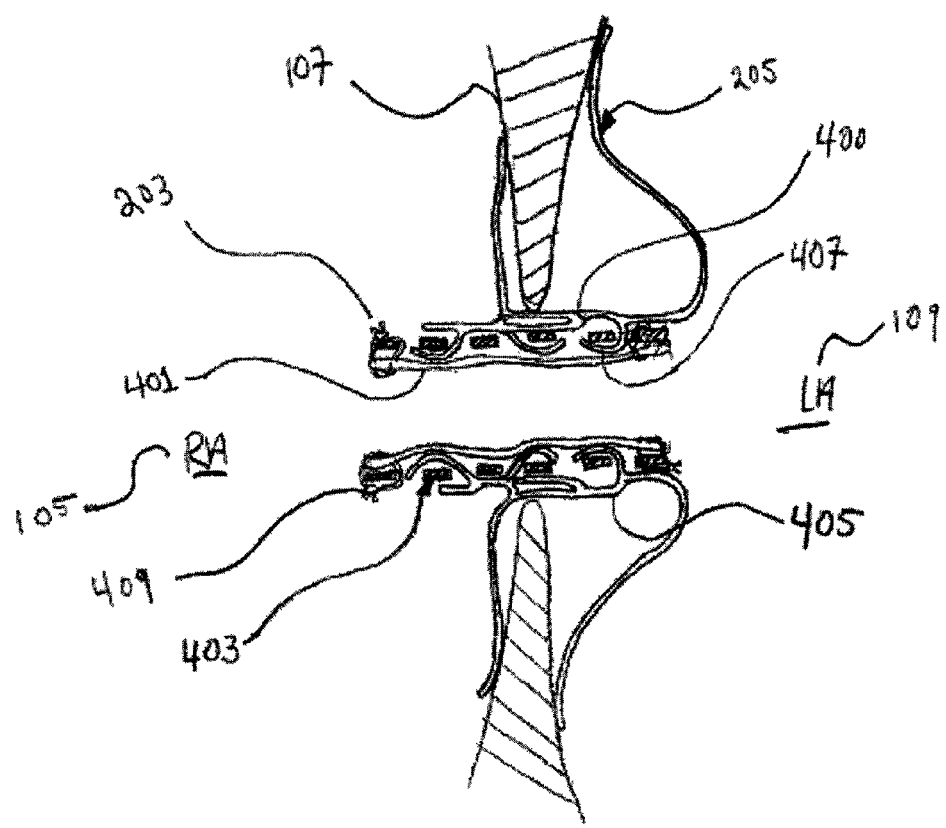

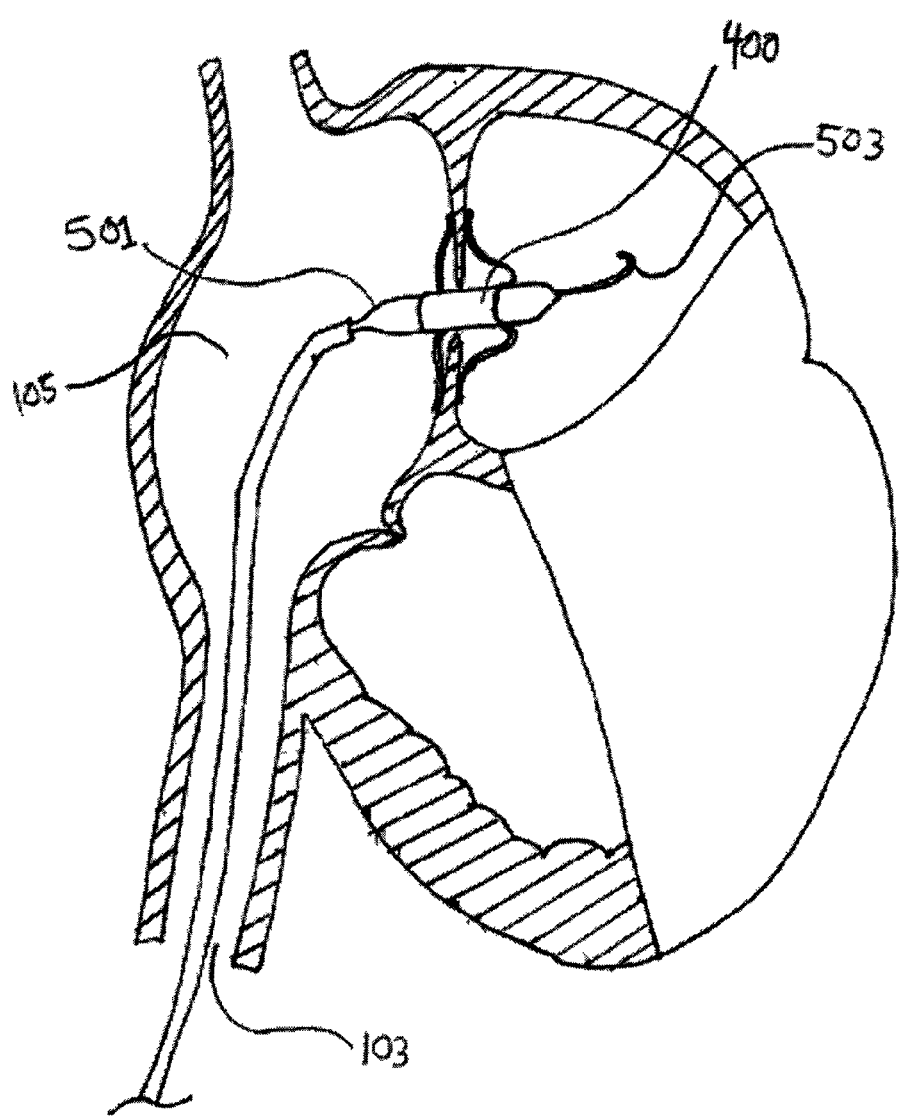

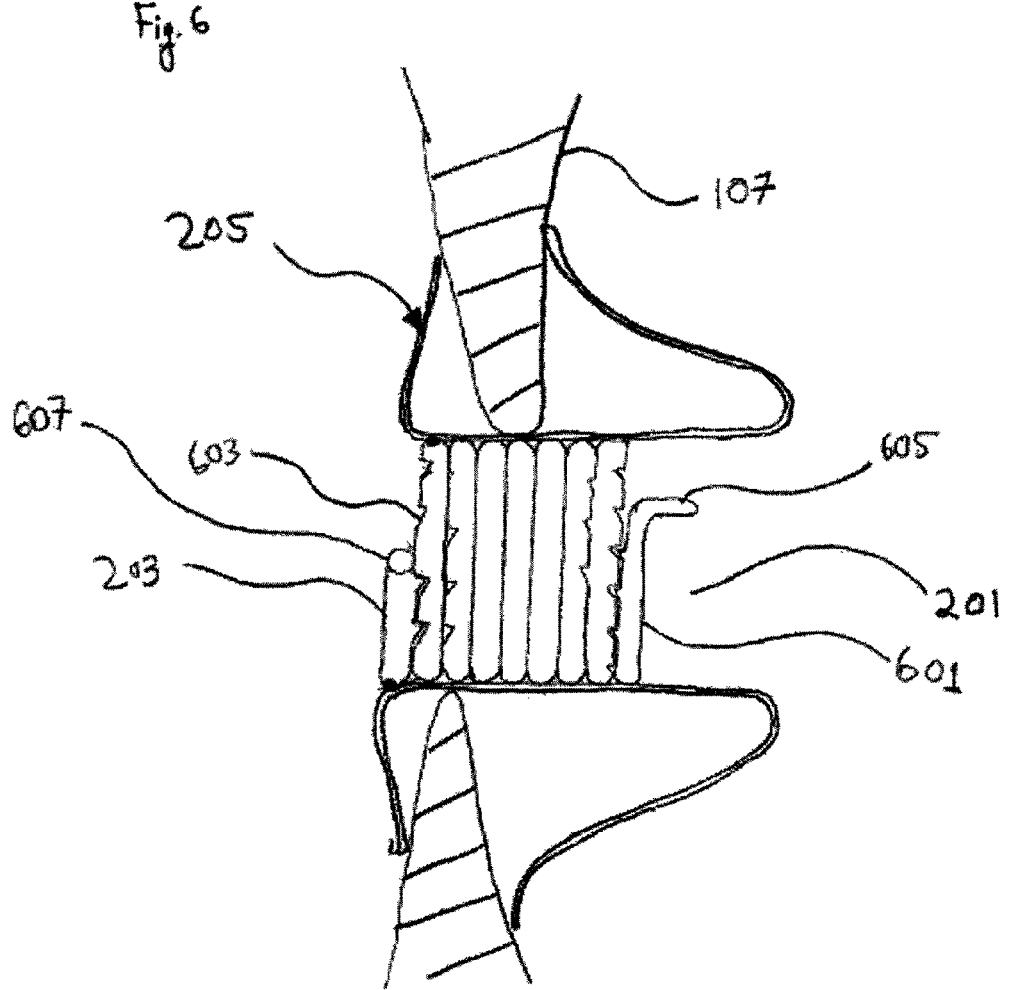

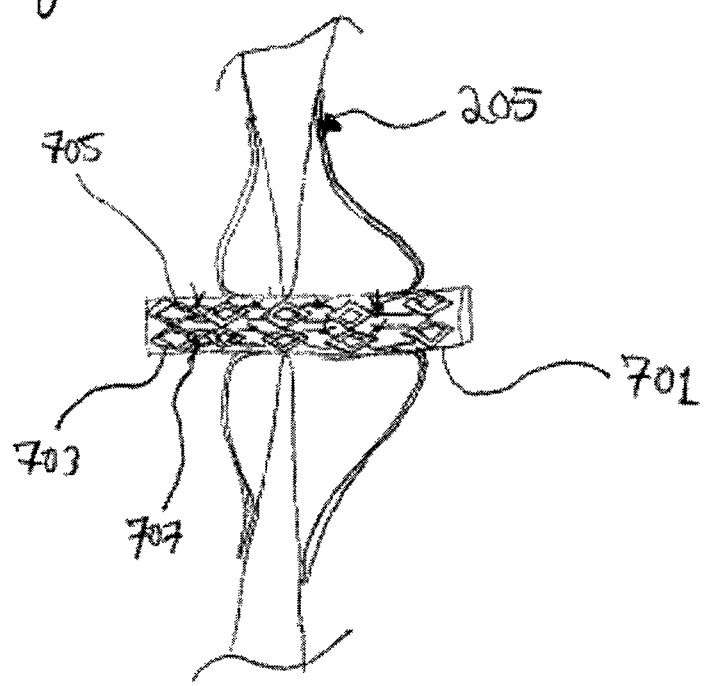

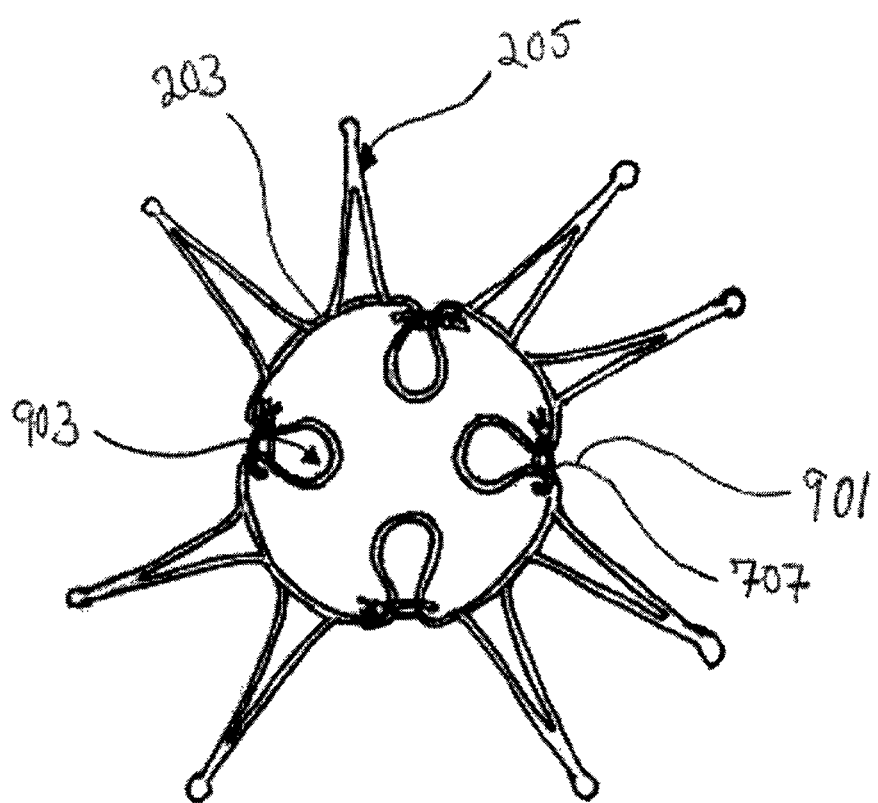

METHODS AND DEVICES FOR INTRA-ATRIAL SHUNTS HAVING SELECTABLE FLOW RATES

CROSS-REFERENCE TO RELATED APPLICATIONS

This application is a non-provisional of U.S. Provisional Application No. 61/579,426, filed Dec. 22, 2011, entitled "Systems, Methods and Devices for Resizing Intra-Atrial Shunts" and of U.S. Provisional Application No. 61/659,520, filed Jun. 14, 2012, entitled "Adjustable Intra-Atrial Shunts", both of which are incorporated by reference herein in their entireties.

FIELD OF THE INVENTION

The present invention relates to methods and devices for treating heart failure. In particular, the present invention relates to methods and devices for treating heart failure by reducing elevated blood pressure in a heart chamber by creating a pressure relief shunt. Additionally, the present invention relates to methods and devices for customizing, adjusting or manipulating the flow of blood through the shunt in order to enhance the therapeutic effect of the pressure relief shunt.

BACKGROUND

Heart failure is a condition effecting millions of people worldwide. Heart failure includes failure of either the left side of the heart, the right side of the heart, or both. Left heart failure can lead to elevated pulmonary venous pressure, which may cause respiratory problems, including shortness of breath and exercise intolerance. Left heart failure may be ascribed to a number of causes, including valve disease, systolic failure of the left ventricle, and diastolic failure of the left ventricle. The adverse clinical result of each of these conditions is similar; the heart failure leads to elevated pressure in the left atrium and elevated pressure in the pulmonary veins, impeding proper flow of oxygenated blood through the blood supply. Therefore, there exists a need to treat the symptoms of left heart failure on the body.

Heart failure has been further classified as either systolic heart failure or diastolic heart failure. Diastolic heart failure refers to heart failure that is present without the presence of major valve disease even while the systolic function of the left ventricle is preserved. More generally, diastolic heart failure is failure of the ventricle to adequately relax and expand in order to fill with blood, causing a decrease in the stroke volume of the heart. Presently, there exist very few treatment options for patients suffering from diastolic heart failure. Therefore there exists a need for methods and devices for treating symptoms of diastolic heart failure.

Some types of pressure relief shunts have been used to treat the symptoms of diastolic heart failure. Examples of such types are disclosed in U.S. Pat. No. 8,043,360 and U.S. Published Patent Application No. 2011/0295366 A1. The long term effects of the creation of a pressure relief shunt can vary greatly depending on the amount of blood flow through the shunt. These effects can include the gradual development of hypertrophic pulmonary arteries for cases with significant left to right shunting. The hypertrophy of the pulmonary arteries in turn leads to worsening symptoms of heart failure. At the other end of the spectrum, the long term effect of the creation of a pressure relief shunt may include a gradual decrease in the amount of blood passing through the shunt such that the benefit of the procedure may be reduced or eliminated.

The hemodynamic conditions associated with diastolic heart failure are not static, and attempting to treat the disease with a static pressure relief shunt represents a deficiency in the prior art. For example, if a shunt is sized too large the short term effect of the creation of a pressure relief shunt may include a sudden worsening of heart failure. This phenomenon has been reported in similar procedures for heart failure patients and may be considered a type of rebound stress. Furthermore, if the pressure relief shunt is sized too small the patient may not experience any clinical improvement from the procedure. The size of the pressure relief shunt required for efficacious treatment of diastolic heart failure may be difficult to predetermine, and varies with the condition of the patient and with the state of the underlying disease. With these deficiencies in mind, there still exists a need, among other needs, for an adaptive means of treating diastolic heart failure by creating a clinically effective and safe pressure relief shunt.

Along those lines, deployment techniques exist for creating a pressure relief shunt in the atrial septum and then gradually allowing the shunt to open by slowly deflating a balloon which initially occludes the shunt. For example, the balloon may be gradually deflated over a period of hours our days. This treatment method and apparatus suffers from deficiencies. For example, the requirement to leave a balloon in place in order to gradually open the pressure relief shunt can create significant problems such as the problem of keeping the balloon in place despite the significant pressure differential across the shunt. Furthermore, the requirement to leave a catheter dwelling within the circulation carries significant potential risks, including increased risk of pulmonary embolism, sepsis, sensitization or allergic reaction, and other potentially adverse clinical reactions.

The constantly evolving nature of heart failure represents a significant challenge for the treatment methods currently disclosed in the prior art. Therefore, there is still a need for novel and adaptable methods and devices for treating diastolic heart failure by creating a pressure relief shunt which can be retrieved, repositioned, adjusted, expanded, contracted, occluded, sealed or otherwise altered as required to treat the patient. Furthermore, there exists a need for devices and methods for treating diastolic heart failure which can automatically self-adjust over time either in accordance with the gradual hemodynamic changes associated with heart failure or in anticipation of these changes.

SUMMARY OF THE INVENTION

In general, the present invention concerns treating heart disease by reducing both left atrial and pulmonary venous pressure. To this end, devices and methods are disclosed herein which may include the creation of a pressure relief shunt in the atrial septum or the placing of a device having a changeable hydraulic diameter into an already existing aperture in the atrial septum. Furthermore, devices and methods are disclosed herein which allow for adjusting the pressure relief shunt in response to the natural progression of the patient during the course of treatment. Additionally, devices and methods are disclosed which provide a treatment which may be adjusted to or which automatically adjusts to the changing conditions in the body as a result of the creation of the pressure relief shunt or the presence of the extant atrial septal aperture. Furthermore, devices and methods are disclosed herein which mitigate the risk of acute worsening of heart failure following the creation of a pressure relief shunt or of an extant atrial septal aperture by allowing for gradual increase in the hydraulic diameter of an implanted device after implantation. Devices and methods are disclosed herein which significantly mitigate the risk of later development of pulmonary hypertrophy by implanting a device which gradually decreases hydraulic diameter in size over time or in response to the natural hemodynamic changes in the heart.

In some embodiments of the present invention, an implantable shunting device is provided. The inventive device includes a pair of anchors, each comprising a plurality of segments, that are adapted to hold the device in place within a membrane wall, e.g. the atrial septum, and a shunting section adapted to permit fluid flow across the membrane wall first at first rate and then at a second rate at a later selectable time.

In some embodiments, the implantable shunting device is adapted to be manually adjusted to change the rate of fluid flow therethrough. For example, the inventive device may include an element which causes the hydraulic diameter of the shunting section to be manually alterable. Such elements may include a coil which may be incrementally wound, stretched, and/or compressed to selectively alter its hydraulic diameter. Such elements may include a tube that can be plastically deformed to alter its hydraulic diameter.

In some embodiments, the implantable shunting device is adapted to automatically change the rate of fluid flow therethrough. For example, the inventive device may have a first configuration which allows a predetermined flow rate to communicate from a high pressure region to a low pressure region across a membrane wall and be adapted to transform over a predetermined period of time into one or more other configurations in order to allow a different flow rate or different flow rates to communicate from the high pressure region to the low pressure region. The transformations may be gradual or may occur in discrete steps or may be a combination of gradual change with abrupt changes. The flow rate changes may be positive or negative or may alternate between the two.

In some embodiments, the implantable shunting device is to permit manual adjustment of the fluid flow rate through the device. For example, in some embodiments, the inventive device includes a hollow tubular body and a number of septal anchoring members, which anchor the inventive device to the atrial septum. The tubular body may be configured with an originally-deployed diameter (a first diameter) which may be expected to provide an efficacious treatment for an average patient. Alternatively, the first diameter of the tubular body may initially be undersized such that an effective treatment may be achieved in some subset of patients while the risk of acute worsening of heart failure following the implantation of the shunt is substantially decreased among all patients. The inventive device is further configured to be manually expanded or contracted by an adjustment device to second, third, fourth, . . . , etc. diameters (also referred to herein as "subsequent diameters"). The inventive device may include interlocking features which maintain the internal diameter that is set by the adjustment device. Alternatively, the tubular body of the inventive device may be made from an elastically deformable, heat setting, pressure-sensitive, or otherwise malleable material such that the diameter of the device remains stable after being set by the adjustment device.

In some embodiments, the inventive device includes an elongate tubular body, an internal member having an orifice, and a number of anchoring members for anchoring the tubular body to the atrial septum. The tubular body further includes an internal fastening feature which releasably clasps the internal orifice-containing shunt member. The internal orifice-containing member has an internal diameter which is configured to allow a therapeutic amount of blood to flow through the shunt. The internal member may be released from the fastening feature of the tubular body with a special retrieval tool and may then be repositioned or replaced with another internal shunt member. The replacement internal shunt member may feature a substantially larger or substantially smaller internal diameter, thus causing the device to have a different subsequent diameter than the first diameter. This replacement of the internal member may therefore be used to adjust the amount of blood flow through the shunt in order to respond to hemodynamic changes in the heart.

In some embodiments, the inventive device including a tubular body and a number of anchoring members is disclosed, where the tubular body may be configured such that its first diameter initially allows only a small volume of blood to shunt from the left atrium to the right atrium. The tubular body may then be designed to gradually expand over the course of days, weeks, or months, to subsequent diameters that allow a larger volume of blood to pass through the shunt. The shunt may be configured so that the internal portion or orifice will expand to a predetermined final subsequent diameter in order to allow a therapeutic amount of blood flow through the shunt. In such embodiments, the orifice of the inventive device may be configured to expand slowly so that the risk of acute worsening of heart failure that may be caused by a sudden hemodynamic change is substantially reduced.

In some embodiments, the inventive device includes a tubular body and a number of anchoring members and is configured to open to an internal diameter that allows sufficient blood to flow through the shunt in order to reduce the left atrial and pulmonary venous pressure. The tubular body may be configured such that over time the internal diameter of the shunt gradually contracts. The internal diameter of the inventive device may be designed to shrink to a predetermined final diameter. The predetermined final diameter may be sized to allow some clinically relevant blood flow through the shunt while simultaneously eliminating the risk of developing hypertrophic pulmonary arteries. Alternatively, the inventive device may be configured such that given enough time the internal diameter becomes completely occluded and blood flow through the shunt is prevented.

In some embodiments, the inventive device featuring a tubular body and a number of anchoring members may be configured to, at first, gradually open the first internal diameter of the shunt and then much later gradually close the subsequent internal diameter of the shunt. The gradual shrinking or expanding of the inventive device is used to control the amount of blood through the shunt in anticipation of the hemodynamic changes that occur over time due to the progression of heart failure and due to the creation of a pressure relief shunt. In still other embodiments the gradual opening or closing of the inventive device may include prolonged periods of static blood flow. For example, the inventive device may be implanted with a small diameter, then over time expand to a second larger diameter and remain there for some period of time. The delay may allow for additional testing or observation by health care personal. After the static delay period the inventive device may be allowed to further expand to a still larger third diameter.

In some embodiments of the present invention, the inventive device including a tubular body and a number of anchoring members may be implanted into an atrial septum. The tubular body of the inventive device includes an anchoring or clasping feature which can be used by a physician to close the inventive device if desired.

In some embodiment, an adjustable intra-atrial shunt includes a retainer having a plurality of struts and a plurality of apices joining the struts to form a generally cylindrical body having a left retaining flange and a right retaining flange, the tubular body adapted to fit within a wall of an atrial septum, the left retaining flange adapted to fit within a left atrium of a heart and the right retaining flange adapted to fit within a right atrium of a heart. The adjustable intra-atrial shunt also includes a removable and/or removable/replaceable insert for placement within the retainer, the insert comprising a generally tubular body having a longitudinal opening to allow a flow of blood from an area of high pressure of the heart to an area of low pressure of the heart and a retrieval loop for removal of the insert from the retainer and the atrial septum, wherein the removable/replaceable insert and the opening allow a first rate of blood flow from an area of high pressure of the heart to an area of low pressure of the heart, and wherein the adjustable intra-atrial shunt is adapted to allow a second rate of blood flow from an area of high pressure of the heart to an area of low pressure of the heart by replacing the removable/replaceable insert with a second removable/replaceable insert having an opening of a different size.

In some embodiments, an adjustable, intra-atrial shunt includes a retainer having a plurality of struts and a plurality of apices joining the struts to form a generally cylindrical body having a left retaining flange and a right retaining flange, the tubular body adapted to fit within a wall of an atrial septum, the left retaining flange adapted to fit within a left atrium of a heart and the right retaining flange adapted to fit within a right atrium of a heart of a patient. This embodiment also includes a removable/replaceable insert for placement within the retainer, the insert comprising a plurality of flaps mounted on a generally cylindrical body having at least one opening to allow a flow of blood from an area of high pressure of the heart to an area of low pressure of the heart, wherein the removable/replaceable insert and the at least one opening allow a first rate of blood flow from an area of high pressure of the heart to an area of low pressure of the heart when first implanted into a patient, and wherein the removable/replaceable insert is adapted to allow a second rate of blood flow from an area of high pressure of the heart to an area of low pressure of the heart after portions of the insert absorb into the patient.

In some embodiments, an adjustable, intra-atrial shunt includes a retainer having a plurality of struts and a plurality of apices joining the struts to form a generally cylindrical body having a left retaining flange and a right retaining flange, the tubular body adapted to fit within a wall of an atrial septum, the left retaining flange adapted to fit within a left atrium of a heart and the right retaining flange adapted to fit within a right atrium of a heart of a patient. This embodiment also includes a removable/replaceable insert for placement with the retainer, the insert comprising at least one flap mounted on a body having at least one opening to allow a flow of blood from an area of high pressure of the heart to an area of low pressure of the heart, wherein the insert and the at least one opening allow a first rate of blood flow from an area of high pressure of the heart to an area of low pressure of the heart when first implanted into a patient, and wherein the insert is adapted to allow a second rate of blood flow from an area of high pressure of the heart to an area of low pressure of the heart after at least one portion of the insert absorbs into the patient.

In some embodiments, methods for treating diastolic heart failure are disclosed. The methods include implanting an inventive device into the atrial septum in order to decrease the left atrial and pulmonary venous pressure. The methods further include measuring the patient's hemodynamic status and heart failure indicators. Finally, the method includes adjusting the amount of blood flow through the inventive device in order to more effectively treat the heart disease. In some embodiments the methods for treating heart failure may include closing the inventive device, expanding the inventive device, collapsing the inventive device, or exchanging either the entire shunt or some components of the inventive device in order to increase the efficacy of the procedure.

BRIEF DESCRIPTION OF THE DRAWINGS

The present invention will become more fully apparent from the following description and appended claims, taken in conjunction with the accompanying drawings. Understanding that these drawing merely depict exemplary embodiments, they are, therefore, not to be considered limiting. It will be readily appreciated that the components of the present invention, as generally described and illustrated in the drawings herein, could be arranged and designed in a wide variety of different configurations. It is to be kept in mind that each of the drawings presented herein is a schematic drawing that may only depict some of the features of the subject matter it is being used to describe.

FIG. 4 is cross-sectional view of an embodiment of an implantable device which has been implanted within an aperture in the atrial septum.

FIG. 5 is a partially cross-sectional view of a patient's heart as in FIG. 4 in which a catheter having a balloon extends through the implantable device.

FIG. 6 is partially cross-sectional view of an embodiment of an implantable device which has been implanted within an aperture in the atrial septum.

FIG. 7 is partially cross-sectional view of an embodiment of an implantable device which has been implanted within an aperture in the atrial septum.

FIG. 9 is an end view of an embodiment of an implantable device.

DESCRIPTION OF PREFERRED EMBODIMENTS

Figure 1:
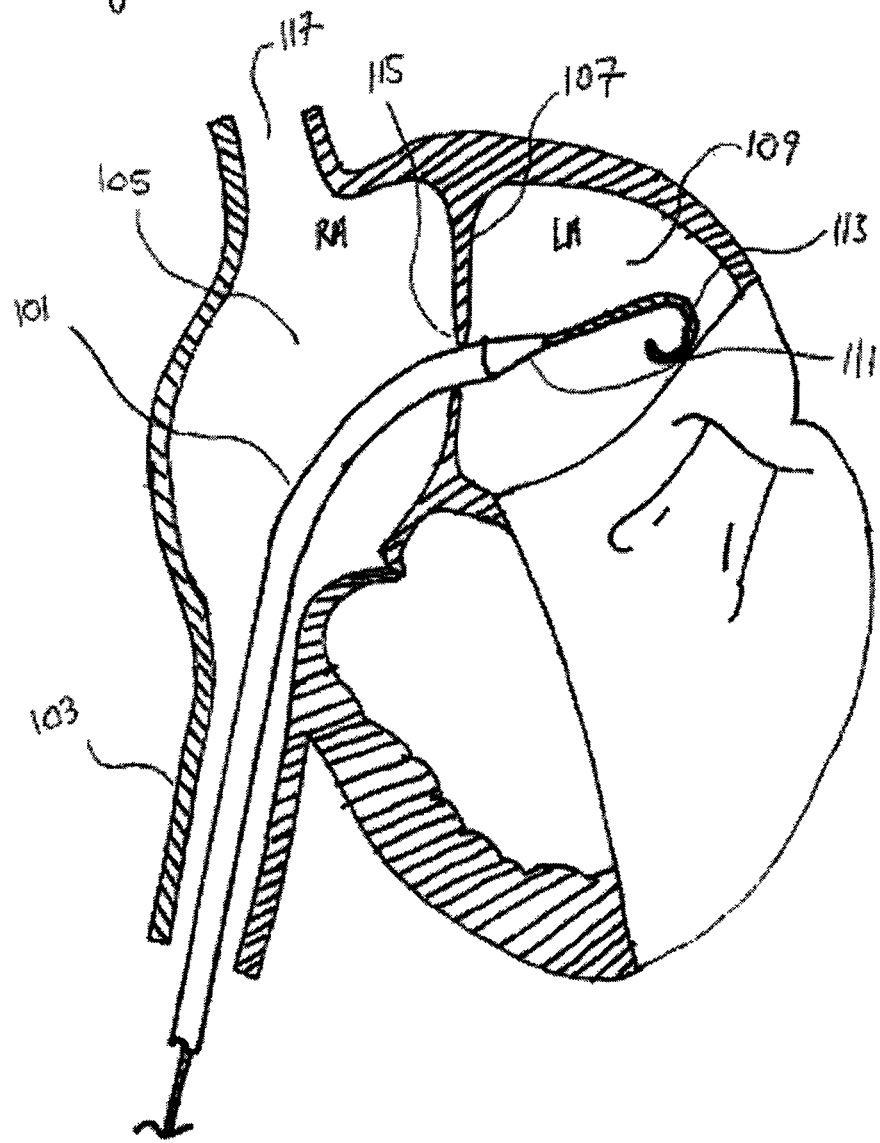
FIG. 1 is a partially cross-sectional view of a patient's heart in which a catheter is extending through the atrial septum.

Certain specific details are set forth in the following description and FIGS. to provide an understanding of various embodiments. Those of ordinary skill in the relevant art will understand that they can practice other embodiments without one or more of the details described below. Further, while various processes are described herein with reference to steps and sequences, the steps and sequences of steps are not be understood as being required to practice all embodiments of the present invention.

Unless otherwise defined, explicitly or implicitly by usage herein, all technical and scientific terms used herein have the same meaning as those which are commonly understood by one of ordinary skill in the art to which this present invention pertains. Methods and materials similar or equivalent to those described herein may be used in the practice or testing of the present invention. In case of conflict between a common meaning and a definition presented in this document, latter definition will control. The materials, methods, and examples presented herein are illustrative only and not intended to be limiting.

Certain specific details are set forth in the following description and FIGS. to provide an understanding of various embodiments. Those of ordinary skill in the relevant art will understand that they can practice other embodiments without one or more of the details described below. Further, while various processes are described herein with reference to steps and sequences, the steps and sequences of steps are not be understood as being required to practice all embodiments of the present invention.

Unless expressly stated otherwise, the term "embodiment" as used herein refers to an embodiment of the present invention.

Unless a different point of reference is clear from the context in which they are used, the point of reference for the terms "proximal" and "distal" is to be understood as being the position of a practitioner who would be implanting, is implanting, or had implanted a device into a patient's atrial septum from the right atrium side of a patient's heart. An example of a context when a different point of reference is implied is when the description involves radial distances away from the longitudinal axis or center of a device, in which case the point of reference is the longitudinal axis or center so that "proximal" refers to locations which are nearer to the longitudinal axis or center and "distal" to locations which are more distant from the longitudinal axis or center.

As used herein, the terms "subject" and "patient" refer to any animal, such as a mammal like livestock, pets, or humans. Specific examples of "subjects" and "patients" include, but are not limited, to individuals requiring medical assistance, and in particular, requiring treatment for symptoms of heart failure.

As used herein, the term "pressure differential" means the difference in pressure between two points or selected spaces; for example between one side of a flow control element and another side of the flow control element.

As used herein, the term "embolic particle" means any solid, semi-solid, or undissolved material, that can be carried by the blood and cause disruption to blood flow when impacted in small blood vessels., including thrombi.

As used herein, the terms "radially outward" and "radially away" means any direction which is not parallel with the central axis. For example, considering a cylinder, a radial outward member could be a piece of wire or a loop of wire that is attached or otherwise operatively coupled to the cylinder that is oriented at some angle greater than 0 relative to the center longitudinal axis of the cylinder.

As used herein, the term "axial thickness" means the thickness along an axis parallel to the center longitudinal axis of a shape or component.

As used herein, the term "axial direction" means direction parallel to the center longitudinal axis of a shape or component.

As used herein, a "sealable connection" is an area where components and/or objects meet wherein the connection defines provides for an insubstantial leakage of fluid or blood through the subject area.

As used herein, the term "lumen" means a canal, duct, generally tubular space or cavity in the body of a subject, including veins, arteries, blood vessels, capillaries, intestines, and the like.

As used herein, the term "sealably secured" or "sealably connected" means stably interfaced in a manner that is substantially resistant to movement and provides resistance to the flow of fluid through or around the interface.

As used herein the terms "bio-resorbable" and "bioabsorbable" refer to the property of a material that allows it to be dissolved or absorbed in a living body.

As used herein, the term "hydraulic diameter" means the overall flow rate capacity of a conduit taking into consideration the number and configuration of the inlets and outlets of the conduit.

As used herein, the terms "gradual" and "gradually" mean that something occurs over the course of time, either in a stepwise fashion or a continuous fashion. For example, the hydraulic diameter of an inventive device may gradually change in a step-wise fashion from an initial value to a later different value when an absorbable suture that initially restrains a geometrical change in the device breaks during its absorption and is no longer able to restrain the geometrical change. As another example, the hydraulic diameter of an inventive device may gradually change in a continuous fashion when an absorbable diaphragm having an initial orifice is continuously absorbed over time so that the diameter of the orifice continuously increases in diameter.

As used herein, the term "whole multiple" means the product contains no decimal.

It is to be understood that whenever relational numbers are used herein, e.g., "first," "second," etc., they are used for convenience of description and so they are to be interpreted with regard to the particular embodiment or claim in which they are presented, rather than as applying globally throughout this document to all embodiments or all claims. Thus, for example, in one embodiment it may be more convenient to use the term "first flange" to describe a flange that would be located in the right atrium when the device of that embodiment is implanted in an atrial septum, whereas it might be more convenient to use the term "first flange" in another embodiment to refer to refer to a flange that would be located in the left atrium when the implantable device of that embodiment is implanted.

It is to be understood that all flow rates are compared at identical the pressure differentials and fluid characteristics. Thus, whenever a device or a portion of a device is said to be adjustable from a first flow rate to a second flow rate, it is to be understood that the hemodynamic conditions under which those flow rates occur are identical to one another.

It should be appreciated that embodiments are applicable for use in other parts of the anatomy or for other indications. For instance, a device such as that described in this disclosure could be placed between the coronary sinus and the left atrium for the same indication. Also, a pressure vent such as is described in this disclosure could be placed between the azygous vein and the pulmonary vein for the same indication.

It is also to be appreciated that although liners or internal sheaths to assist in directly fluid flow through the inventive device are described below with regard to only some of the embodiments, the other described embodiments may be adapted to include the use of liners or internal sheaths.

The present invention may include a percutaneously deliverable device. In some embodiments, the device has a straightened, elongated, low-profile delivery configuration suitable for delivery via a delivery system. The device may have a generally radially expanded and sometimes shortened deployed profile. For example, it can have a distal anchoring portion positioned on the left atrial side of the septum, a right anchoring portion positioned on the right atrial side of the septum, and/or a shunt portion, sometimes referred to as a "core segment", positioned through an aperture in the septum. The anchoring portions are sometimes referred to herein as "flanges". A flange may be annular flanges. An annular flange may comprise a plurality of segments. It is to be understood that in some embodiments having right and left anchors that the anchors may be connected and in some embodiments they are integrally connected.

In some embodiments, when a device according to the present invention is deployed across a patient's atrial septum, the distal and proximal flanges are located left and right to the septum respectively. The core segment of the device creates a shunt or passageway allowing blood flow across the aperture. Generally, the left atrium has a higher pressure than the right atrium and the blood tends to flow from the left atrium across the shunt to the right atrium. The greater the cross-sectional size of the core segment at any point in time, i.e., its shunting size, the greater amount of blood flows from the left to right atria. The greater the amount of blood flows to the right atrium, the greater the left heart decompresses. The left atrial pressure can be measured directly with a catheter in the left atrium or indirectly by measuring the pulmonary capillary wedge pressure (PCWP) during a right heart catheterization. The normal values of the mean left atrial pressure are typically in the range of 6-12 mmHg. The shunting size of the core segment of devices of the present invention may be tailored so that, during and post implantation, the left atrial pressure would reach the normal range of 6-12 mmHg. Thus for a DHF patient having a significantly elevated left atrial pressure, a device with a bigger shunting size should be used to restore the left atrial pressure to the normal range. For a DHF patient with a moderately elevated left atrial pressure, a device with a smaller shunting size should be used to restore the left atrial pressure.

The left atrial v-wave is the left atrial pressure at the end of an atrial diastole but immediately before the opening of the mitral valve. The left atrial v-wave represents the peak of the left atrial pressure. The size of the left atrial v-wave is determined partially by the amount of blood entering the left atrium. The normal range of left atrial v-wave is 6-21 mmHg. The shunting size of the core segment of the devices of the present invention may be tailored so that the left atrial v-wave would reach the normal range of 6-21 mmHg. Thus, for a DHF patient with significantly elevated left atrial v-waves, a device with a bigger shunting size can be used to restore the v-wave to the normal range. For a DHF patient with moderately elevated left atrial v-waves, a device with a smaller shunting size should be used to restore the v-wave to the normal range.

Systematic oxygen saturation is routinely monitored during a percutaneous implantation procedure. With the decompression of the left heart, the shunting size of the core segment of devices of the present invention may be tailored so that the systemic oxygen saturation level during and/or after an implantation procedure is maintained in the range of 75-100%. For a DHF patient with an elevated left atrial pressure, the higher the left atrial pressure elevation is prior to a treatment, the greater the shunting size should be used to maintain the systemic oxygen saturation level at a safe range; and the lower is the left atrial pressure elevation is prior to a treatment, the smaller the shunting size should be used to maintain the systemic oxygen saturation level at its safe range.

The ratio of pulmonary blood flow to systematic blood flow is defined as a Qp:Qs ratio. In a healthy heart, the Qp:Qs ratio is 1:1. In a DHF patient, Qp:Qs ratio is generally greater than 1:1. Some go beyond 2.5:1. The devices of the present invention be used to restore the Qp:Qs ratio to or close to the normal range. Thus, the left-to-right flow produced by the device may be tailored so that the Qp:Qs ratio would at some time reach the acceptable range of 1:1 to 1.5:1.

The greater the left-to-right shunting flow which is generated by the device, the lesser amount of blood remains inside the left atrium and, later, enters the left ventricle. The smaller is the shunting flow, the greater amount of blood remains inside the left atrium and, later, enters the left ventricle. The normal values of mean left ventricle pressure are typically in the range of 40-80 mmHg. Thus, the shunting size of the core segment of the device may be tailored so that the left ventricle pressure would reach the normal range of 40-80 mmHg. For a DHF patient with a significantly elevated left ventricle pressure, a device with a bigger shunting size may be used to restore the left ventricle pressure to the normal range. For a DHF patient with a moderately elevated left ventricle pressure, a device with a smaller shunting size may be used to restore the left ventricle pressure to the normal range.

With the left-to-right shunting flow created by the device, the amount of blood inside the right atrium increases, which results in an elevated right atrium pressure. The greater the left-to-right shunting flow is, the greater is the amount of the blood that remains inside the right atrium, and in turn, the greater is the elevation in the right atrial pressure. The smaller the left-to-right shunting flow is, the lesser is the amount of the blood that remains inside the right atrium, and in turn, the lesser is the elevation in the right atrial pressure. The normal values of the mean right atrial pressure are typically in the range of 4-12 mmHg. Thus, the shunting size of the core segment of the device may be tailored so that the right atrial pressure would remain the range of 4-12 mmHg. Thus for a DHF patient with the right atrial pressure in the lower range, such as in the range of 4-6 mmHg, a device with a bigger shunting size can be used, and for a DHF patient with the right atrial pressure within the higher range, such as in the range of 10-12 mmHg, a device with a smaller shunting size should be used to prevent right atrium overload.

With the left-to-right blood flow created by the device, the amount of blood inside the right atrium increases, and the amount of blood entering into the right ventricle increases, which results in an elevated right ventricle peak systolic pressure. The greater is the left-to-right shunt, the greater is the amount of blood remains inside the right atrium, and in turn the greater is the amount of blood enters into the right ventricle, and the greater is the elevation in the right ventricle peak systolic pressure. The lesser the left-to-right shunt, the lesser is the amount of blood remains inside the right atrium, and in turn the lesser is the amount of blood enters the right ventricle, the lesser is the elevation in the right ventricle peak systolic pressure. The normal values of the mean right ventricle peak systolic pressure are typically in the range of 20-40 mmHg. Thus, the core segment of the device may be tailored so that the right ventricle peak systolic pressure would not exceed the normal range of 20-40 mmHg. Thus for a DHF patient with the right ventricle peak systolic pressure within the lower range, such as in the range of 20-30 mmHg, a device with a bigger shunting size could be used; and for a DHF patient with the right ventricle peak systolic pressure within the higher range, such as in the range of 30-40 mmHg, a device with a bigger shunting size should be used in order to prevent right ventricle overload.

With the left-to-right blood flow created by the shunt device, the amount of blood remaining inside the right atrium increases, and in turn, the pressure difference between the right and left atrium decreases. The greater is the left-to-right shunt, the greater is the amount of blood remains insider the right atrium and the greater reduction in the pressure difference between the left and right atria. The smaller is the left-to-right shunting flow, the lesser amount of blood remains inside the right atrium and the lesser reduction is in the pressure difference between the left and right atria. The normal values for the pressure difference between the left and right atria are typically in the range of 2-10 mmHg. Thus, the shunting size of the core segment of the device may be tailored so that the pressure difference between the left and right atria would not exceed the range of 2-10 mmHg. Thus for a DHF patient with a pressure difference between the left and right within the lower range, such as in the range of 2-5 mmHg, a device with a bigger shunting size can be used. For a DHF patient with a pressure difference between the left and right atria within the higher range, such as in the range of 5-10 mmHg, a device with a smaller shunting size should be used in order to prevent right atrium overload.

FIG. 1 depicts a schematic view of a patient's heart and shows an example of a delivery catheter. An implant delivery catheter sheath 101 is shown extending from the inferior vena cava (IVC) 103, through the right atrium 105, across the atrial septum 107, and finally into the left atrium 109. By convention the left atrium is depicted on the right side of FIG. 1, and the right atrium is depicted on the left side of FIG. 1. This convention will be used throughout this document. In essence, the heart of FIG. 1 represents a simplified view of a patient's heart. A conical dilating catheter 111 extends from the distal end of the delivery sheath while a crossing wire 113 further extends out of the dilating catheter. The implant delivery catheter is shown having crossed the atrial septum at the region of the fossa ovalis 115, where the atrial septum is very thin.

The implant delivery catheter of FIG. 1 is configured to house an inventive device implant. The conical dilating catheter of FIG. 1 is configured to move axially within the implant delivery catheter, such that the conical surface may be initially used to dilate a small hole in the atrial septum and then may later be advanced or retracted in order to facilitate the deployment of the inventive device implant. The transition 117 between the dilator and the sheath is carefully designed such that a very minimal step exists between the two components.

The crossing wire of FIG. 1 may be any suitably stiff wire currently available for catheter procedures, or it may be custom made for the procedure. The wire may include a sharpened tip in order to more easily perforate the septum. The wire may be made of stainless steel, Nitinol, or any other suitable material. After crossing the septum the wire may be withdrawn from the body, or may be left behind in order to facility the advancement of further devices and catheters into the body. In addition the wire may feature a curved distal section (as shown) in order to prevent the user from accidentally puncturing the wall of the left atrium. In embodiments of the present invention, the guide wire is a 0.9 mm (0.035") J-curve Nitinol wire. In other embodiments of the present invention the guide wire may be similar to the wires used in the treatment of total coronary occlusions. The design, manufacture, and use of guide wires for penetrating tissue are well known in the art.

The dilation catheter of FIG. 1 may be manufactured in a number of ways, and may be made of any suitable biocompatible material. A simple dilation catheter might be made from LDPE, HDPE, or FEP, and may feature a heat formed or over-molded conical tip. Another suitable dilation catheter construction might include a PEBAX or nylon braided shaft with a specially designed conical cap. The dilation catheter features a generally circular cross-section, however ridges or texturing may be employed in order to more efficiently dilate the septum by creating localized stress-concentration in the tissue near the ridges. In addition, the distal conical section of the dilator may incorporate a number of cutting features, such as a small metallic blades, or sharpened plastic protrusions, in order to more effectively dilate the atrial septum. In some embodiments of the present invention, the OD of the dilator is roughly between 3 mm and 5 mm.

Still referring to FIG. 1, the dilation catheter extends from an access point (not shown) in the lower veins, and extends into the right atrium through the inferior vena cava. In alternative embodiments of the present invention the dilation catheter may access the atrial septum by other means, including from the jugular vein (not shown) and through the superior vena cava 119. In addition, access to the atrial septum may be provided by other means, including through minimally invasive surgery, and through other major vessels in the body.

Continuing to refer to FIG. 1, the delivery catheter may be configured such that in order to deploy a inventive device implant (not shown) the user may simply advance the catheter to the approximate position shown in the FIG. and then retract the sheath relative to the dilator, thereby exposing the implant to the tissue. The dilator and guide wire may then be withdrawn from the atrial septum, leaving behind the therapeutic implant. Alternatively, the dilator may be withdrawn from the sheath and the sheath may then be used as a conduit for advancing a simple delivery catheter. The inventive device delivery catheter may be configured to carefully expand the left atrial side of the shunt in the left atrium with the sheath in place in the atrial septum. The sheath may then be withdrawn and the delivery catheter may be further configured to allow the right atrial side of the implant to expand in order to fully deploy the interatrial inventive device. The implant may be configured such that it is collapsed into a delivery configuration featuring a small delivery diameter and then naturally expands into the implanted configuration featuring a larger implanted diameter.

It is to be understood that the delivery catheter described with regard to FIG. 1 is only an example of a delivery catheter that can be used with the inventive devices. After extraction, the inventive device would be drawn into the catheter for removal. The inventive devices may also be used with other delivery catheters known in the art. Examples of delivery catheters are disclosed in U.S. Published Patent Application No. 2011/0295366 A1.

Figure 2:
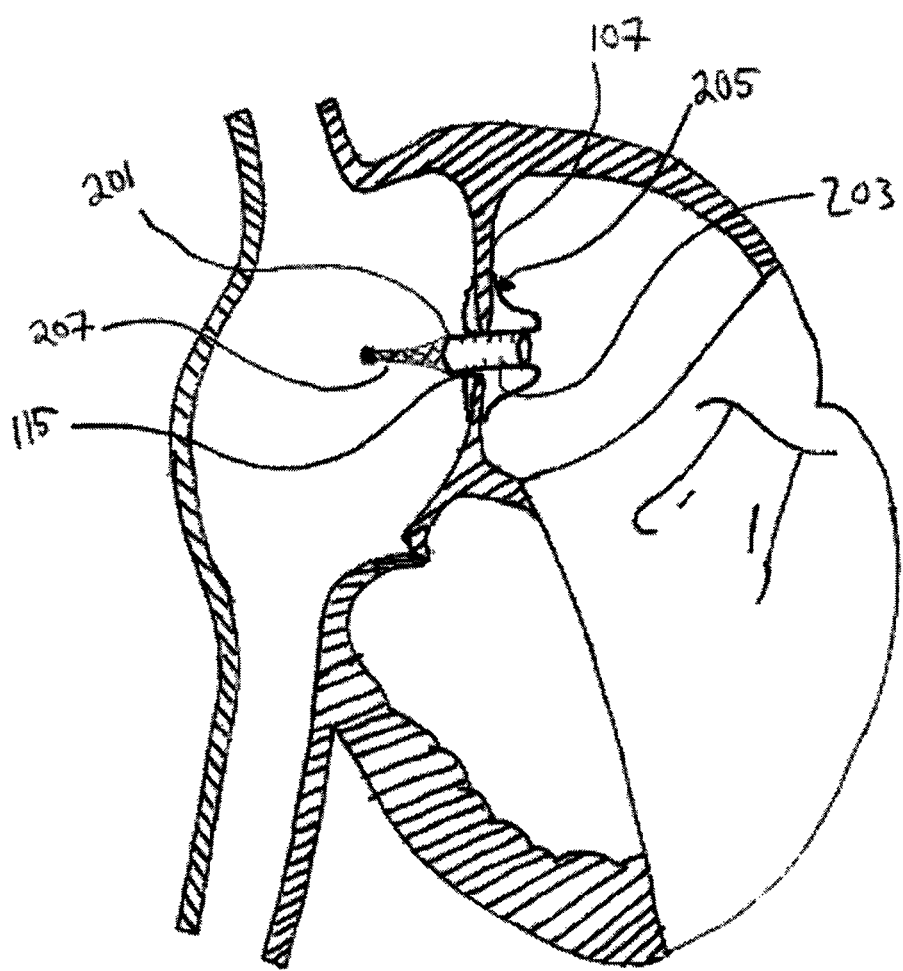
FIG. 2 is a partially cross-sectional view of a patient's heart in which an embodiment of an implantable device has been implanted within an aperture in the atrial septum.

Referring now to FIG. 2, an inter-atrial inventive device 201 is depicted as implanted into the atrial septum 107. The inventive device includes a tubular body 203 and a series of anchoring elements 205. The anchoring elements are designed to extend from the tubular body and engage the tissue of the atrial septum near the fossa ovalis 115. A conical tail 207 extends from one end of the shunt out into the right atrium. The conical tail has a very open mesh-like structure such that it does not impede blood flow through the shunt even though it connects to the tubular body circumferentially. The tubular shunt is configured to allow blood to flow through the internal diameter of the tubular body, thereby acting as a means to limit the pressure differential across the atrial septum.

Still referring to FIG. 2, the tubular body of the inventive device may be made of any suitable biocompatible implant material. The tubular body may include a stent-like skeleton, which may be collapsible to facilitate delivery of the device. The tubular body may further include an internal or external sheath in order prevent blood from flowing around the device instead of through the internal diameter of the shunt. The stent-like skeleton of the tubular body may be made of a laser-cut Nitinol tube, or may instead be made of woven Nitinol wire. The stent member may instead be made of stainless steel, MP35N, Cobalt-chromium, other shape-memory type alloys, other materials referred to as super-elastic alloys, or a plastic or polymeric material. Methods of manufacture of stents and stent-like implants are well established in the relevant prior art.

The conical tail of the interatrial shunt of FIG. 2 is configured such that it extends into the right atrium and therefore represents a feature which could be engaged by an appropriate retrieval catheter. The retrieval of the interatrial shunt is depicted in FIG. 3.

Figure 3:
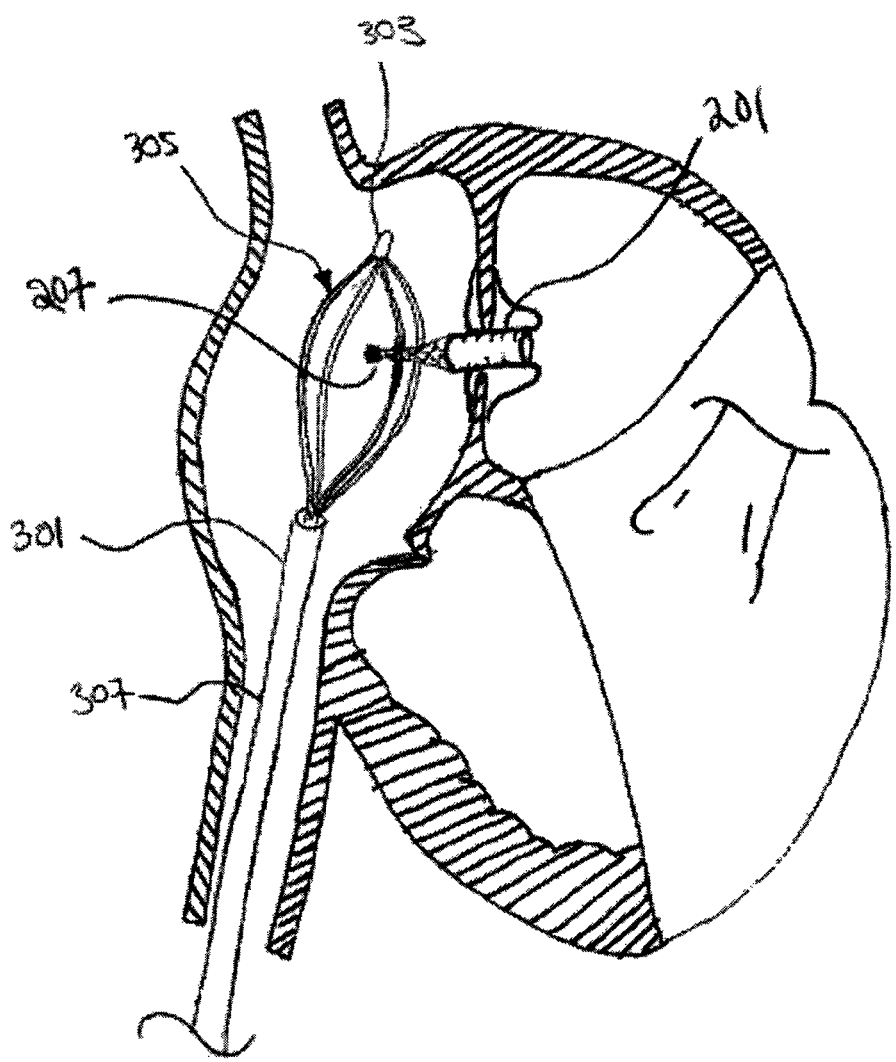
FIG. 3 is a partially cross-sectional view of a patient's heart as in FIG. 2 in which a catheter with a retrieval device is poised to engage the conical tail of the implantable device.

Referring now to FIG. 3 a snaring catheter 301 is shown having been positioned near the conical tail 207 of the interatrial inventive device 201. The catheter consists of a radio-opaque tip 303, a series of basket-wires 305, and a delivery sheath 307. The snare may be opened or closed by respectively retracting or advancing the delivery sheath. Advancing the delivery sheath over the basket-wires causes them to collapse into the sheath, while retracting the delivery sheath away from the basket-wires allows the wires to return to their open configuration. In this way a user is able to snare the conical tail of the inventive device by advancing the snaring catheter into the right atrium near the inventive device and retracting the delivery sheath exposing the basket-wires. The basket-wires would then expand in a way that makes entanglement with the conical tail very likely. The user may then re-advance the delivery sheath and capture the conical tail. The user may then withdraw the catheter from the body, in turn pulling the interatrial shunt out of the atrial septum. In this way the snaring catheter represents a retrieval catheter and may be used to remove an implanted interatrial shunt. Once this step is completed the user may then implant a new shunt of a larger or smaller internal diameter, or may instead replace the shunt with an occluding device, or may otherwise seal the hole in the septum. In this way the implant of FIG. 2 and the retrieval device of FIG. 3 represent a system for adjusting the inventive device in order to allow for the treatment of a progressing or otherwise changing disease state.

FIG. 4 depicts a sectioned view of an embodiment of the present invention featuring an adjustable inventive device 400 as implanted into an interatrial septum 107. The inventive device of FIG. 4 includes an elongate tubular body 203 and a series of anchoring members 205. The elongate tubular body is constructed in roughly concentric layers. The inner most layer is an optional internal liner 401 which directs the blood flow through the device from the left atrium 109 into the right atrium 105. The next layer is a stent like body 403 which is manufactured of a plastically deformable material. This layer is represented in cross-section as a series of rectangular cross-hatched regions. The plastically deformable stent like member is constructed from a material such as stainless steel, and is designed such that when expanded, contracted, or otherwise deformed to a desired diameter it will naturally remain in the deformed state. The outer most layer of the tubular body of FIG. 4 is a super-elastic layer 405 from which the anchoring members extend. The super-elastic layer has a number of hook features 407 which couple the elastic layer to the plastically deformable layer. The super-elastic layer may be manufactured by laser-cutting a nitinol hypotube and then shape-setting the hooks and anchoring members into the desired shape. A series of knotted sutures 409 are shown connecting the innermost layer, i.e., the internal liner 401, and the plastically deformable layer, i.e., stent like body 403; however the individual layers may be connected by any suitable means in order to form a cohesive tubular shunt body. It is to be understood that although for the sake of clarity the internal liner 401 is shown as being attached only at its ends to the stent like body 403, the internal liner 401 may be attached at any and all points along its length to either the stent like body or the super-elastic layer 405.

The layered construction of the tubular body of FIG. 4 allows for a user-adjustable shunt to be created. The user may adjust the size of the shunt by first engaging the shunt and then by deforming the plastically deformable layer as desired. The deformation is frozen in place by the plastically deformable layer. This deformation is then transferred to the super-elastic layer and the internal layer because the layers are interconnected and because the plastically deformable layer is stiffer than the other two layers. An example of such a manipulation is shown in FIG. 5.

Referring to FIG. 5, an adjustable pressure-relief shunt 400 similar to that which is described above is shown. The pressure-relief shunt is being expanded by a balloon catheter 501. The balloon catheter extends from the inferior vena cava 103 into the right atrium 105 and through the shunt. A guide wire 503 extends from the balloon catheter and may be used to initially cross the shunt and then provide a rail for the dilation catheter placement. The balloon catheter may be inflated with a radio-opaque die in order to allow for precise control of the deformed diameter of the interatrial shunt. The dilation balloon may be a carefully sized non-complaint balloon. Alternatively, the dilation balloon may be a complaint balloon and the inflation pressure may be carefully controlled in order to achieve the desired shunt diameter. In some embodiments the adjustable inventive device is configured with an initial diameter around 3 to 4 mm and may be safely expanded up to 10 mm.

In embodiments the adjustment of the inventive device of FIG. 5 might begin with an echocardiography analysis of the blood flow through the shunt and an analysis of the patient's diastolic pressure, total cardiac output, pulmonary arterial pressure, and pulmonary venous pressures. If it is determined that the shunt should be adjusted the user might then carefully select the appropriately sized balloon. After gaining access to the vascular anatomy by conventional techniques a user may advance a guide wire into the right atrium and carefully direct the wire through the inventive device. The guide wire may then be used as a rail and the selected balloon may then be positioned inside the interatrial shunt. The balloon would then be carefully inflated until the desired diameter is achieved. The balloon is then deflated and withdrawn. The user may then repeat the analysis steps and further adjust the diameter of the shunt with additional balloon dilations if desired. In some embodiments of the present invention the initial diameter of the inventive device is configured to be very small such that the initial amount of blood flow through the valve is unlikely to cause rebound stress or shock. The user would then increase the diameter of the shunt as part of a routine follow-on procedure or as a delayed part of the initial implantation procedure.

The deformable and adjustable inventive devices of FIGS. 4 and 5 may be configured to be elastically adjusted by means other than a balloon catheter. For example, a inventive device may be designed such that the internal diameter of the shunt is adjusted by an axial compression or expansion. In other embodiments the shunt may be adjusted by a winding or unwinding action, or by a puckering, folding, or unfolding action.

Turning now to FIG. 6, a further embodiment of the present invention is depicted which may be adjusted in vivo from providing a first flow rate across a membrane of the patient's heart, e.g., the atrial septum, to having a second flow rate. The second flow rate may be selected as the result of evaluating the patient's heart condition at a time after the implantation of the device An interatrial shunt 201 is shown as implanted into an atrial septum 107. The interatrial shunt is comprised of a tubular body 203 and a series of fastening members 205. The tubular body of FIG. 3 is formed by a tightly wound coil 601. The interface between the coils at either end of the tubular body features a series of one directional ramps 603. On the left atrial side of the tightly wound coil is a left side adjustment tang 605 and on the right atrial side of the tightly would coil is a right side adjustment tang 607. The adjustment tangs encroach into the internal diameter of the shunt in order to allow for the user to engage the adjustment tangs with an appropriate adjustment catheter.

The tightly wound coil 601 of FIG. 6 may be made of any of the materials mentioned above, including nitinol, stainless steel, or a polymeric material. The fastening members 205 may be connected to the coil at one end of the device such that the majority of the coils are able to be manipulated and repositioned relative to the tissue fastening members. Alternatively, the adjustment coil 601 may be configured to rotate independently of the fastening members while simultaneously being axially constrained relative to the fastening members 205. Finally, the fastening members 205 may be connected to a separate tubular body which lies within and is constrained by the tightly wound coil 601.

The tightly wound coil 601 of FIG. 6 together with the one directional ramp features and the adjustment tangs 605, 607 allow the user to adjust the internal diameter of the shunt 201 by winding or unwinding the coil. For example, the user may use an appropriate adjustment catheter to engage the adjustment tangs 605, 607 of the interatrial shunt 201, and then apply torque to the right adjustment tang 607 relative to the left adjustment tang 605. The effect of this rotational adjustment would be to unwind the coil, 601 which in turn opens the internal diameter of the interatrial shunt. The ramp features 603 allow for the unwinding motion of the coils, but lock this motion in place, preventing the coils to return to their normal state. If the user wishes to reverse this operation the ramps 603 may be circumvented by separating or stretching the coils axially, thereby over-riding the ramp features 603. The number of turns of the coil 601 is carefully configured such that the coil represents enough length such that it is longer than septum's thickness in order to shunt the blood from the left atrium to the right atrium. The number of coils is further configured such that a reasonable number of rotations are required to effect a preselected diametrical change in the shunt 201. For example, the number of coils and the initial diameter of the shunt may be configured such that one 360 degree unwinding of the coils increases the diameter by 2 mm. The coil 601 may be configured to create an adjustable inventive device with an internal diameter ranging from roughly 4 mm to 10 mm.

The interatrial shunt 201 of FIG. 6 is configured to be implanted by an appropriate delivery catheter. The interatrial shunt is configured to collapse into the catheter either by increasing the number of winds and thereby decreasing the diameter, or by unwinding the coil 601 and straightening the wire. The exact configuration of the interatrial shunt in its collapsed configuration depends on the material and design of the coil. For example, if the tightly wound coil is made of a super-elastic nitinol wire then the coil may be completely unwound and advanced through a catheter with a very small internal diameter. The super-elastic properties of the nitinol coil would allow the user to then advance the wire through the catheter, which would recover its initial coiled configuration upon exiting the catheter tip. For a stainless steel coil it would be more appropriate to conFig. the coil to be delivered in a first collapsed diameter. The user would then deliver the interatrial shunt by implanting it into the tissue and then deforming the stainless steel coil with an unwinding motion until the implant reaches a larger second diameter.

The adjustment tangs 605, 607 of FIG. 6 are configured to be engaged or disengaged in vivo in a repeatable manner by an adjustment catheter. The adjustment catheter includes an inner and an outer shaft, each of which is configured to transmit torque relative to the other. For example, the adjustment catheter may include a braided outer catheter shaft and a tri-filar inner catheter torque transmitting shaft. Alternatively the adjustment catheter may include a laser cut hypotube which is designed to transmit torque. The engagement of the catheter with the adjustment tangs may be assisted by the use of radio-opaque markers incorporated within the shunt near the adjustment tangs. The adjustment catheter inner and outer shaft may each feature a slot for engaging with the adjustment tangs. The slots include a generous lead-in in order to help position the catheter. The slots may be tapered to lock the tangs into the adjustment catheter. The adjustment catheter may include an expandable basket or expandable support wires in order to center the catheter within the interatrial shunt. Alternatively the adjustment catheter may incorporate a snaring mechanism to ensnare the adjustment tangs. The inner and outer adjustment catheter shafts may then interact with the snaring features in order to engage the adjustment tangs. Finally, a series of adjustment tangs may be used to create a shape that can be keyed off of by a catheter. For example, the left side of the coil may feature three adjustment tangs which create a clover shaped internal profile in the inventive device. This profile may then be easily engaged by an appropriately shaped adjustment catheter.

In use a physician would advance the adjustment catheter into the internal diameter of the interatrial shunt. The adjustment catheter may be tracked over a wire which has been placed through the shunt and into the left atrium. The left side and right side adjustment tangs 605, 607 would then be engaged by the adjustment catheter using any of the above described engagement methods, including simply keying the tangs into a pair of slots. The left side adjustment tang 605 would be keyed into the inner shaft of the adjustment catheter while the right side adjustment tang 607 would be keyed into the outer shaft of the adjustment catheter. The left side adjustment tang 605 may be held stationary by the inner adjustment catheter shaft, while the outer adjustment catheter shaft would then be rotated by the user in the appropriate direction to unwind the coil 601 and increase the inner diameter of the shunt. Alternatively, the right side adjustment tang 607 may be held stationary by the outer adjustment catheter shaft while the left side adjustment tang 605 is rotated by the inner adjustment catheter shaft. In either case, the fastening features of the inventive device would be connected to the side of the shunt that is held stationary relative to the body. In this way the shunt is not simply rotated within the interatrial septum. In some embodiments the user may be able to reset the coil back to its initial configuration by axially stretching the tightly wound coil and thereby disengaging the one-directional ramps 603 and allowing the coil to wind or unwind as needed.

The adjustable interatrial inventive device of FIG. 6 may be modified to allow for reducing the internal diameter of the inventive device with the adjustment catheter. This may be accomplished by simply reversing the directions of the one-direction ramps 603, such that a winding motion instead of an unwinding motion may be locked in by the one-directional ramps. In this case the shunt may be deployed in a collapsed delivery diameter and then expanded to a first implanted diameter by the user. The user may then decrease the size of the interatrial shunt by winding the coil 601 in a similar manner to that described above. Once again, the user may be able to reset the interatrial shunt to the initial deployed diameter by axially stretching the coils to over-ride the one-directional ramps.

Figure 8A:
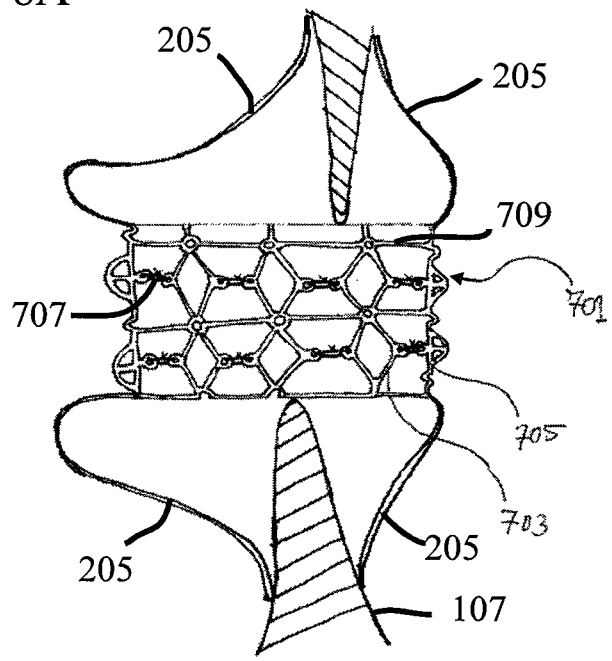
FIG. 8A is a partially cross-section view of an embodiment of an implantable device which is similar to that shown in FIG. 7, except for the alteration to its diamond shaped struts.
Figure 8B:
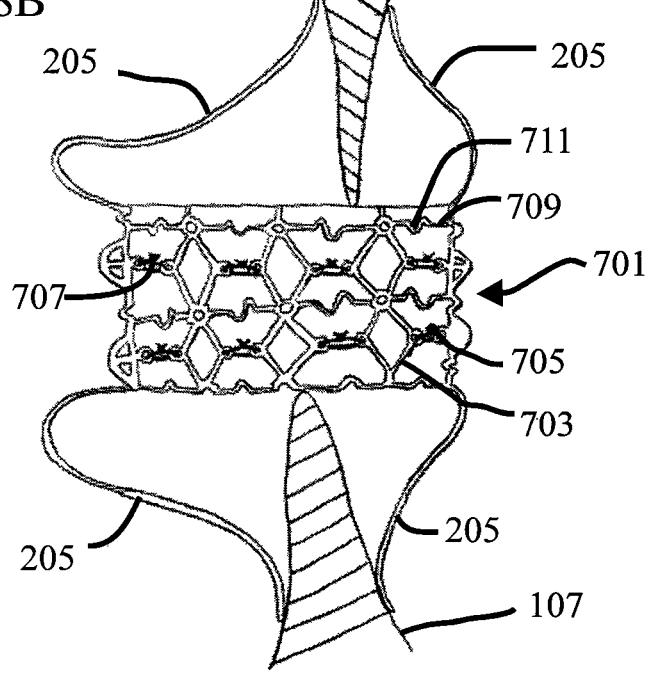
FIG. 8B is a partially cross-section view of an embodiment of an implantable device which is similar to that shown in FIG. 8A, except for the alteration to its axially stiff members.

Turning now to FIGS. 7-8B, alternative interatrial shunts are depicted. The inventive devices illustrated in these drawings are the same as each other except as noted below. The interatrial shunt of FIG. 7 includes a stent-like elongate tubular body 701 and a series of anchoring members 205. The stent-like frame of the tubular body includes a series of diamond shaped struts 703. Each diamond shaped strut features a pair laser cut eye-holes 705. The diamond shaped struts and eye-holes are spaced around the circumference and the length of the stent-like frame. Bio-resorbable suture material 707 is shown tied between various pairs of eye-holes. The suture materials are tied such that the stent is held in an elongated state by the presence of the suture, as the diamond shaped struts are held stretched out axially. The stent frame is therefore shown in an elongated state in FIG. 7. The suture material is designed to be slowly absorbed by the body over time, which in turn allows the diamonds struts to return to their relaxed configuration. The relaxed diamond struts in turn exert a radially outward force, causing the stent member to expand radially as the suture material is absorbed into the body. In this way the inventive device of FIG. 7 represents a means for automatically and gradually changing the amount of blood flow through a inventive device in order to provide a non-static treatment for diastolic dysfunction.

The stent-like frame of may be made from a laser cut nitinol hypotube in a manner that is very similar to the manufacture of many stents. The laser cut nitinol hypotube may then be heat set to a predetermined final diameter. The heat set stent frame may then be stretch axially and then the suture knots tied around the eye-holes of the stent frame. The stent frame features sets off axially stiff members 709 (identified in FIG. 8A) between the various diamond-shaped struts. The axially stiff members are configured to help maintain the integrity of the stent frame such that the force required to stretch the diamond struts axially does not simply collapse the stent frame between the struts. The initial diameter of the stent frame may be configured such that the inventive device allows only a small amount of blood to flow through the shunt. Furthermore, the number, size, and shape of the diamond struts may be carefully selected such that the final diameter of the shunt after the loss of the suture loops reaches a size that allows sufficient blood flow through the shunt to treat the majority of the patient population. Still further, the amount that the diamond shaped struts are stretched may be configured such that a predetermined amount of mechanical advantage is built into the expanding action of the stent frame.

The bio-resorbable sutures of the devices of FIGS. 7-8B may be made from any number of known absorbable suture fibers, including polyglycolic acid, polylactic acid, polydioxanone, or polycaprolactone. The manufacture of bio-resorbable sutures is well known in the art. Absorbable sutures of various sizes may be used to delay or stagger the effect of the expanding action of the inventive device. Bio-absorable sutures may have a diameter ranging from 0.1 mm to 0.7 mm (USP sizes 6-0 to #3 respectively). In addition, the bio-resorbable sutures may be a monofilament construction, or may be braided. The bio-resorbable substrate may instead include a suture-like structure of any cross-sectional geometry, including a film-like structure, a thin tape-like structure, or a rectangular or triangular cross-section. As an example, initially a rapid expansion may be desired and so very thin sutures are used at strategic locations to allow for the initial expansion of the shunt. Subsequently, a much slower expansion may be desired, and this secondary expansion phase may be accomplished by using a much thicker suture material on a second set of expansion struts. The inventive device may be configured to expand gradually from roughly 4 mm to roughly 10 mm over the course of a number of days, weeks, or months.

FIG. 8A shows a more detailed view of the inventive device described with regard to FIG. 7. The action of the eye-holes 705 and the diamond shaped struts 703 can be more clearly seen in FIG. 8A, although the mechanisms are the same as described above. The inventive device of FIG. 8A is shown with a lesser expansion ratio than that of FIG. 7, as the diamond struts are stretched less such that when the sutures are absorbed into the body the shunt will expand less. This may be desirable for patients with toughened septal tissue, as the lesser expansion allows for the use of stiffer diamond struts which are capable of exerting a larger outward radial force. The bio-resorbable suture material may be made from any of the above mentioned materials and may include any of the above mentioned configurations. In addition, the bio-resorbable sutures may be replaced by any other suitable bio-resorbable substrate, including a sheet of bio-resorbable material, a bio-resorbable mesh, or a bio-resorbable film.

Upon sufficient dissolution of the bio-resorbable restraints, the device shown in FIGS. 7 and 8A will bulge radially outward to assume a barrel shape thereby increasing the hydraulic diameter of the device so as to increase the flow rate therethrough. A variation of the device of FIGS. 7 and 8A is shown in FIG. 8B. The device of FIG. 8B is similar in all respects to that of FIGS. 7 and 8A except that it contains expandable sections 711 along its axial stiff members 709. Upon sufficient dissolution of the bio-resorbable restraints, the expandable section 711 cause an increase in the longitudinal length of the body 701 and a corresponding contraction of its diameter, thus decreasing its hydraulic diameter and the flow rate therethrough.

Turning now to FIG. 9, a inventive device 901 is shown as viewed from the central axis of the shunt. The inventive device consists of a tubular body 203 and a series of anchoring members 205 which extend radially outward from the shunt body. The anchoring members again are used to anchor the inventive device to the septum. The tubular body is made of a stent-like frame. An optional internal liner (not shown) may be used to ensure that blood flows through the shunt from the left atrium and into the right atrium instead of through the side wall of the tubular body. The tubular body of the shunt is periodically broken into by a series of inward folds 903 of the tubular body. The inward folds are held in place by bio-resorbable sutures 707 similar to those used in previous embodiments. The inward folds are configured to take up space inside the shunt, and thereby limit the amount of blood flow through the shunt. As the sutures are absorbed into the body the folds are configured to gradually straighten out, and the inventive device is thereby expanded. The expansion by loss of the inward folding is caused both by the direct expansion of the inventive device as well as by the fact that the folds impede blood flow and as they disappear the blood is able to flow through the shunt more efficiently.

Referring now to FIGS. 10A-10D an embodiment of the interatrial inventive device is depicted as it gradually transforms over time. The interatrial shunt of FIGS. 10A through 10D is designed to be implanted with a first effective internal diameter. The shunt is then configured to gradually expand over time to a second, substantially larger effective internal diameter. Finally, after a longer but still predetermined amount of time the inventive device of FIGS. 10A-10D is configured to contract to a third effective internal diameter which is substantially smaller than the second effective internal diameter. It is to be noted that the intra-atrial shunt of the presently invention may be configured to adjust to an multitude of progressively larger or smaller diameters, and thus is not limited to the three progressively larger diameters described in connection with FIGS. 10A-D.

Figure 10A:
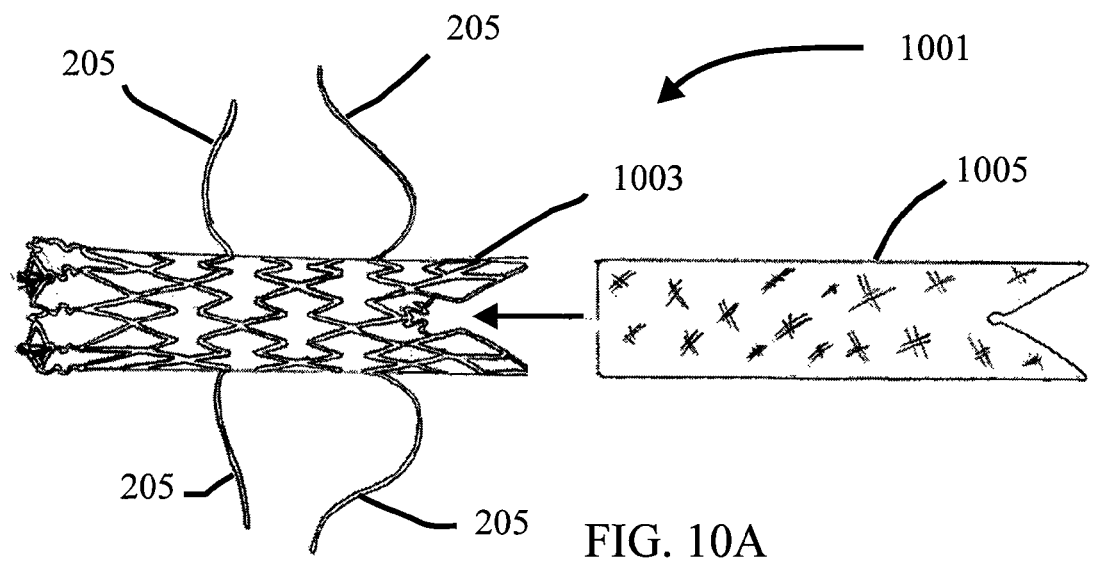
FIG. 10A is an exploded side view of an embodiment of an implantable device.
Figure 10B:
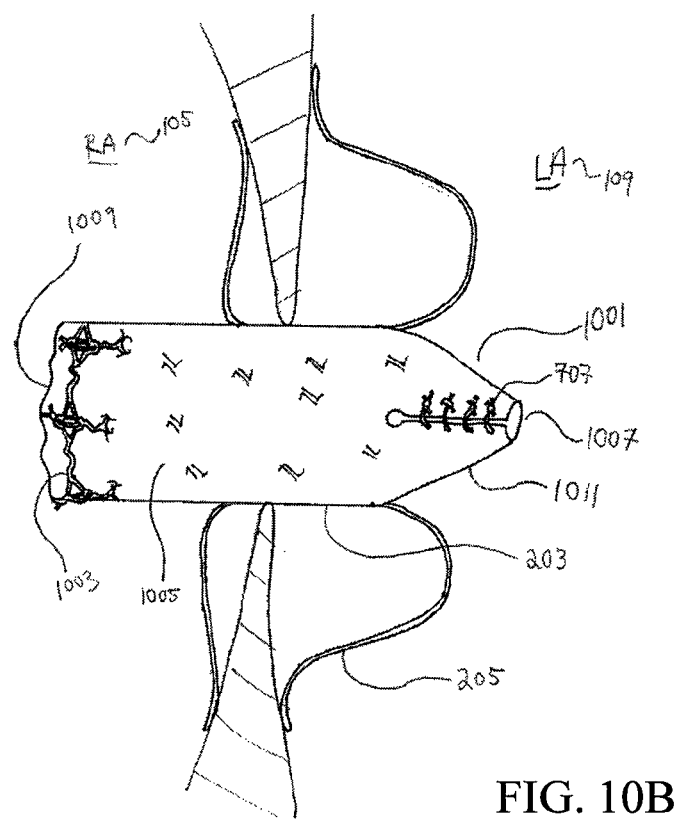
FIG. 10B is partially cross-sectional view of the embodiment of FIG. 10A which has been implanted within an aperture in the atrial septum showing the implantable device just after implantation. Only a small portion of the frame of the device is shown in this drawing.
Figure 10C:
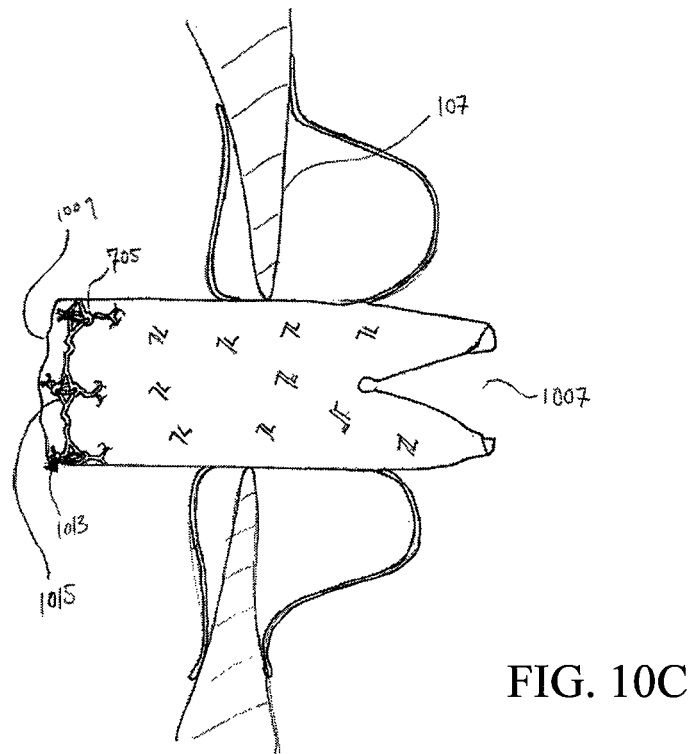
FIG. 10C is a partially cross-sectional view as in FIG. 10A but showing the implantable device at a later time after the absorption of the biosorbable material which at one end of the device. Only a small portion of the frame of the device is shown in this drawing.

FIGS. 10A-D depict another embodiment of inventive device. FIG. 10A shows an exploded side view of interatrial inventive device 1001. The stent-like frame 1003 is shown about to receive the internal sheath 1005 to which it will be subsequently attached. For clarity sake, only a small portion of the frame 1003 is shown in FIGS. 10B-10C.

Referring now to FIG. 10B, an interatrial inventive device 1001 is depicted. The inventive device includes an elongate tubular body 203 and a series of anchoring members 205. The elongate tubular body includes a stent-like frame 1003 and an internal sheath 1005. The stent-like frame is once again constructed from a super-elastic material, such as nitinol. The stent-like frame includes a left end 1007 and a right end 1009, the left end points into the left atrium 109 and the right end protrudes into the right atrium 105. The left end is designed with a conical opening 1011. The conical opening is manufactured by creating a wedge shaped cut out of the tubular frame and folding the frame such that the cut edges are adjacent to each other. The left end of the frame is cut such that the opening is fully open in the relaxed configuration, but has been compressed and sewed as pictured with bio-resorbable sutures 707. The bio-resorbable sutures of the left end are configured to be absorbed by the body over a predetermined period of time. For example, in some embodiments the sutures are designed to be absorbed in 10 to 30 days time. As the sutures dissolve into the body the left end opening is configured to gradually expand, such that the amount of blood flow through the device gradually increases. As the last suture is absorbed into the body the interatrial shunt reaches its maximum diameter. The maximum diameter of the interatrial shunt is carefully configured in order to allow for a therapeutic amount of blood to flow through the device. In some embodiments this maximum diameter may be between 6 mm and 10 mm.

Referring now to FIG. 10C, where the interatrial inventive device of FIG. 10B still with a left end 1007 and a right end 1009 is depicted as implanted into the atrial septum 107. The left end bio-resorbable sutures have dispersed into the body and the internal diameter has reached its peak size. The inventive device is configured to remain at this configuration for a predetermined amount of time. The duration of the shunt remaining at its maximum effective internal diameter is controlled by the right end bio-resorbable substrate. The right end is cut or shape set in a normally closed configuration. The shunt is then expanded and the expansion is locked in place by the bio-resorbable substrate. As shown in FIG. 10C, the bio-resorbable substrate may be a series of bio-resorbable sutures 1013. The sutures are able to hold the right end of the interatrial shunt open due to the structure of the right end stent-like frame, which features a series of diamond shaped struts 1015, similar to those depicted in FIG. 7. The diamond shaped struts are designed such that the major axis of the diamond points along the axis of the device and is much longer than the minor axis of the diamond. On either end of the major axis of the diamond shaped struts are eye-holes 705, through which sutures may be tied. A suture is tied between the two eye holes on the diamond shaped struts and the major axis of the diamond is compressed. This in turn causes the minor axis to expand, with the net result being the expansion of the circumference of the shunt which finally leads to the expansion of the overall diameter of the shunt. The amount of expansion may be controlled by the length of the suture knot, the shape of the struts, or the number of diamond struts that wrap around the circumference of the inventive device. The right sided bio-resorbable sutures are configured to take a much longer time to absorb into the body than the left side sutures. For example, the right side sutures may be made of a USP size #1 suture while the left side bio-resorbable suture may be a USP size 4-0 suture or smaller.

Figure 10D:
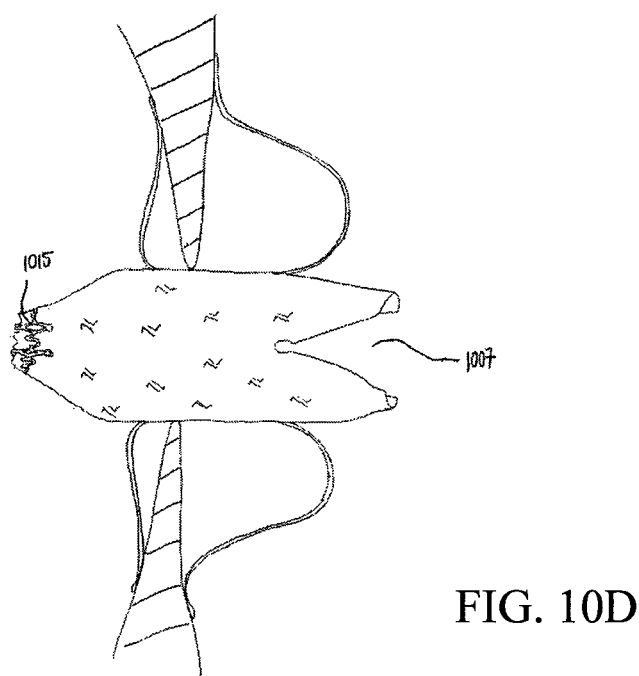
FIG. 10D is a partially cross-sectional view as in FIG. 10C but showing the implantable device at a still later time after the absorption of the biosorbable material at the other end of the device. Only a small portion of the frame of the device is shown in this drawing.

Turning now to FIG. 10D, the interatrial inventive device of FIG. 10B and 10C is depicted in its final configuration, where the left side 1007 has opened up fully, and much later the right side 1009 has closed fully. The diamond shaped struts 1015 are shown in the relaxed configuration and the right side is overall at its lowest energy state. The size of the final right side orifice may be configured such that a minimum amount of blood is allowed to flow through the device such that some therapeutic treatment may be expected of the shunt without the risk of the adverse events of associated with significant long term left to right shunting of blood. In this way FIGS. 10A-D represent a means for treating diastolic heart failure dynamically.

Figure 11:
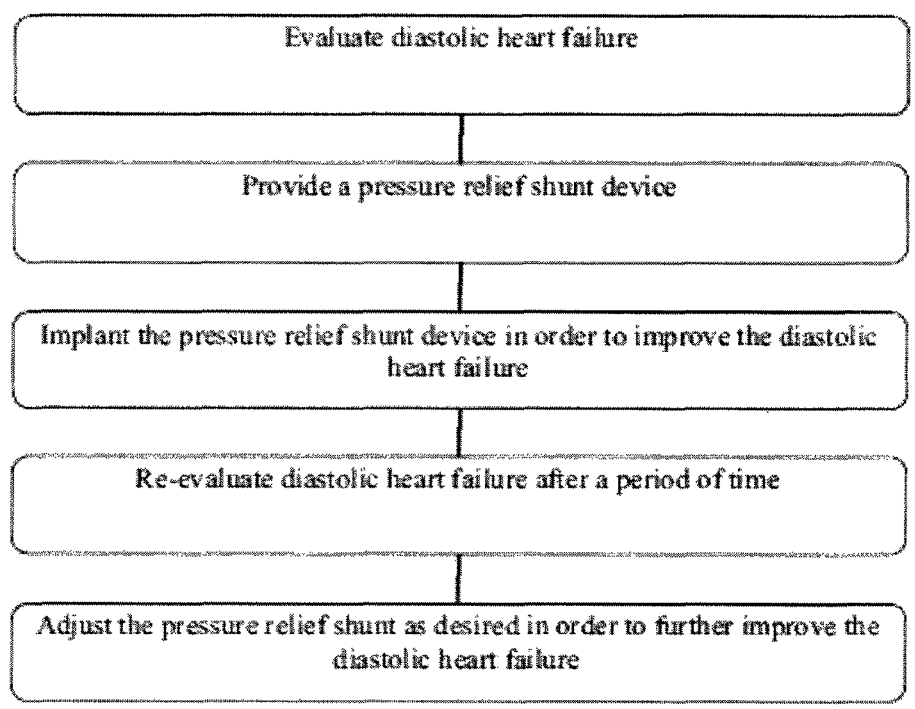
FIG. 11 is a flow diagram of a method embodiment.

Turning now to FIG. 11, a method for treating diastolic heart failure is outlined. The method includes first analyzing or characterizing the patient's diastolic dysfunction through means that are well described in the art, including trans-esophageal echocardiography, trans-thoracic echocardiography, MRI, CT, or catheterization. The method further includes using the data gained from the analysis to select a inventive device to be implanted into the interatrial septum with a preselected internal diameter. The inventive device may be any of the adjustable inventive devices described herein or any of their equivalents. The inventive device is configured to allow an amount of blood flow through the shunt that is determined by the analysis to be unlikely to cause any short term shock or pressure spikes for the patient. The method then includes a waiting period where the patient's heart is given time to gradually adjust to the newly improved hemodynamic conditions. Next a second series of analysis is then carried out, using similar methodologies to those described above. The second analysis is used to determine whether additional adjustment of the shunt would be beneficial for the patient. If the adjustment is thought to be beneficial based on the analysis then the method includes using an appropriate adjustment catheter or adjustment balloon catheter to adjust the inventive device and thereby change the amount of blood flow through the shunt in order to benefit the patient. The adjustment may include increasing the internal diameter of the inventive device in order to allow additional blood flow through the device or it may instead include decreasing the diameter of the shunt in order to prevent complications such as the development of hypertrophic pulmonary arteries. In this way the method outlined in FIG. 11 represents a method for treating diastolic heart failure in a dynamic and adjustable manner.

While the foregoing description focused on embodiments that automatically adjust the flow rate through the shunt, the present invention also includes embodiments which the flow rate adjustment is made manually or a combination of manually and automatically. Some embodiments which may include automatic, manual, or a combination of automatic and manual rate adjustments are described below.

Figure 12:
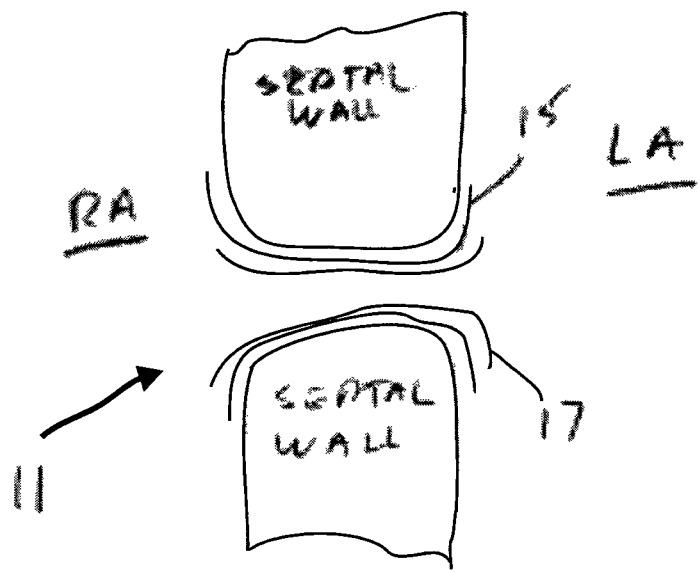
FIG. 12 is a cross-sectional view of an embodiment of an implantable device after implantation in an aperture of an atrial septum.

This disclosure concerns an adjustable shunt for allowing flow from an area of high pressure, such as a left atrium of a heart, to an area of lower pressure, such as a right atrium of a heart. As explained above, this device may help to relieve over-pressure and may aid in preventing hypertrophy in the affected blood vessels. FIG. 12 discloses a cross-section of a multi-part intra-atrial shunt 11 placed into a septum and held in place by the septal wall of a person's heart. The shunt 11 includes two parts, a retaining cage 15 directly attached to the septal wall, and an insert 17 attached to the cage 15 and retained in place by the cage. In this embodiment, the shunt 11 may be relatively symmetrical, i.e., the portion of the shunt retained in the left atrium is substantially similar to the portion of the shunt retained in the right atrium. In addition, the tubular central portion may be relatively uniform along its length.

Figure 13:
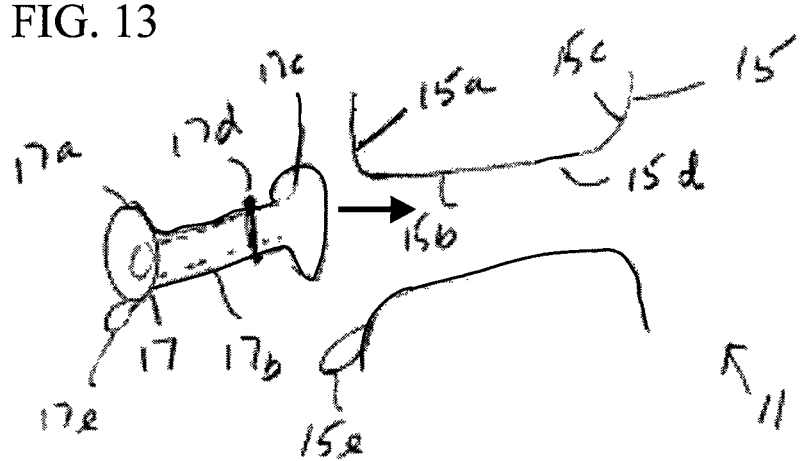
FIG. 13 is a partially exploded view of the inventive device of FIG. 1

A closer and more detailed view of a shunt embodiment is disclosed in FIG. 13. In this embodiment, the shunt 11 includes cage 15 and insert 17, the cage and the insert also including retaining features that allow the insert to reversibly lock into the retaining cage. Cage 15 includes a right atrium flange 15a which is substantially similar to left atrium flange 15c. The intermediate portion 15b is substantially tubular, with a retention feature 15d, which may be a void or a space, i.e., an indentation or some other receptacle, available on the outer surface of the cage. Cage 15 may be made of struts and apices of nitinol, the nitinol having a martensite/austenite transition below 37° C., preferably in the neighbourhood of about 25° C., so that the cage remains in its superelastic, austenitic phase during use inside a body of a human or a mammal.

The other portion of the adjustable shunt is the insert 17, which may be impermeable and may allow flow of blood or other fluid only through its central passage. Insert 17 includes an outlet 17a and an inlet 17c that is substantially similar to the outlet. The central portion 17b is generally tubular and not permeable to fluids, with an outer surface having a retention feature 17d for matching with the retention feature 15d of cage 15. Insert 17 may be formed from a polymer such as PTFE, UHMWPE, HDPE, polypropylene, polysulfone, or other biocompatible plastic.

Retention feature 17d may be a tab or a button for placing into a void or space of cage 15. It will be understood by those having skill in the art that the inner diameter or dimension of insert 17 determines blood flow from the higher pressure left atrium to the lower pressure right atrium of the patient into whom the shunt is implanted. It will also be understood that the cage 15 will be implanted first with the insert 17 later implanted into the cage. Both the cage and the insert have a removal feature 15e, 17e, such as a loop of suture or of a radiopaque material included into the retrieval loop. Examples of radiopaque materials may include a gold or platinum thread. A retrieval device, such as a snare or grasper, may be used to grasp the retrieval loop for removal from the patient or re-placement within the patient.

The retention feature is important because the insert will only control the flow of blood from an area of higher pressure to an area of lower pressure in the heart if it is retained in place. The retention feature is also important because it is this feature that allows the purposeful or intentional removal of the insert, so that the insert can be replaced with an insert of a lesser or greater diameter, depending on whether a lesser or greater amount of pressure relief is required for the patient. As noted above, the amount of relief, that is, the radius or hydraulic radius of the opening, may vary among patients and may vary in time for a given patient. Thus, a multi-part shunt, with inserts of different effective hydraulic diameters, may be used to allow relief to a patient. To be clear, it is to be understood that a multi-part shunt may include a plurality of inserts and one insert may be replaced by another in vivo as need be to achieve the desired flow rate for the patient. It is clearly a less traumatic surgical procedure to replace the insert described here than to implant the entire shunt, and in particular, to implant the cage. Once the cage has been implanted, subsequent procedures are accomplished more quickly and with less trouble to the patient. The inserts, for example, may have inner diameters from 0 to 15 mm, including inserts having inner diameters from 3 to 5 mm. This is the diameter of the flow path from a higher pressure area to a lower pressure area.

Figure 14:
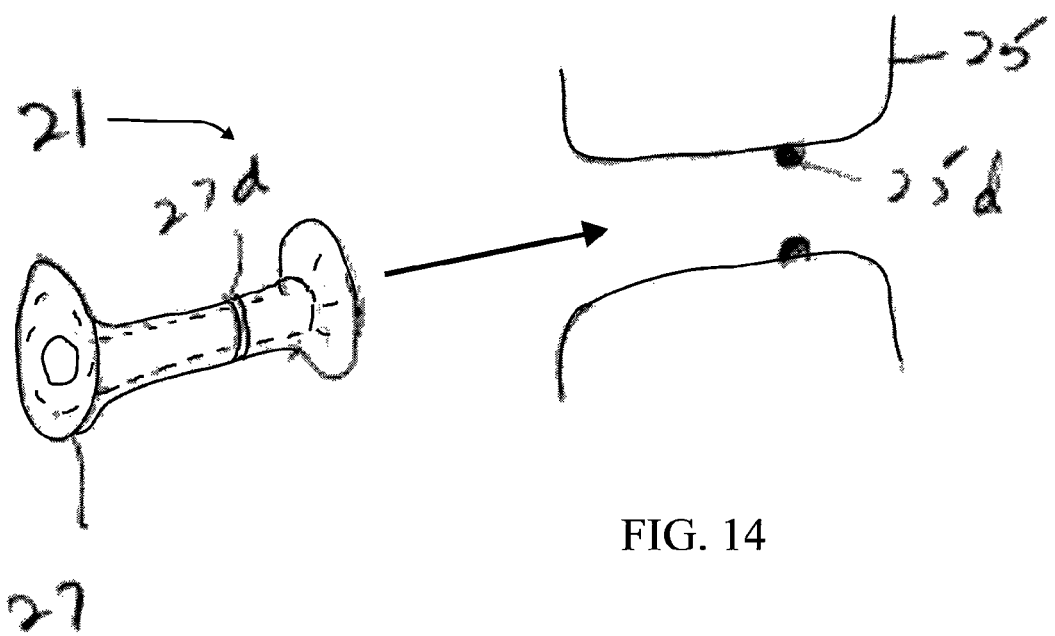
FIG. 14 is a partially exploded view of another embodiment of an implantable device.

Another embodiment is depicted in FIG. 14. In this embodiment, adjustable intra-atrial shunt 21 includes a cage 25 with a positive or protruding retention feature 25d, such as protruding tab or ridge on its inner side. Insert 27 includes a groove 27d to receive the protruding rib or ridge from the cage 25. Thus, the insert is retained within the cage.

Figure 15:
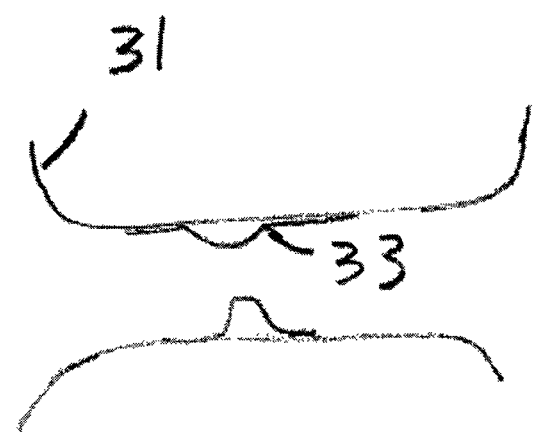
FIG. 15 is a cross-sectional view of the insert portion of an embodiment of an implantable device.

In another embodiment depicted in FIG. 15, insert 31 includes an inner portion of reduced diameter 33, the portion with reduced inner diameter molded to that shape or produced by one or more secondary operations. Using this technique, a single insert shell or form may be used and then adapted or adjusted to the desired shape. For example, an inner form with the reduced diameter may be bonded to the inside of a standard shell by solvent bonding, ultrasonic welding, or other technique. This allows producers to have one or more basic insert shapes that may then be individualized using a series of forms, or third parts. In one embodiment, the inner diameter is reduced to zero, so that an attending physician or medical professional may entirely close the shunt, preventing blood flow altogether between the left and right atria.

Figure 16:
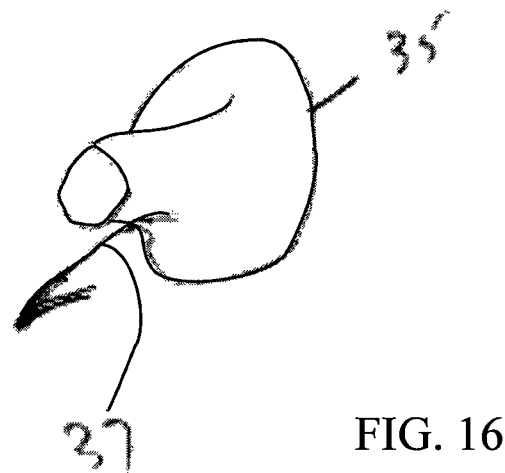
FIG. 16 is a perspective view of an insert portion of an embodiment of an implantable device.
Figure 17:
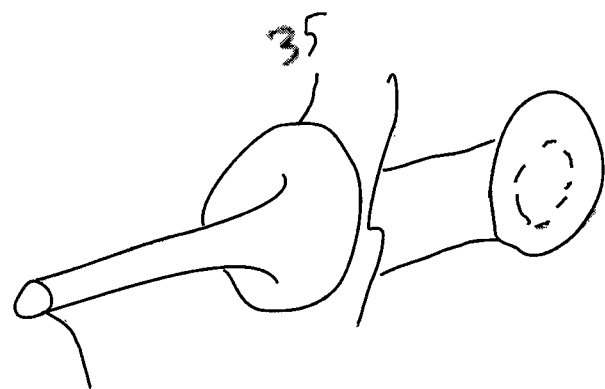
FIG. 17 is a perspective view of an insert portion of an embodiment of an implantable device.

It is desirable that the inserts and cages be retrievable, as noted above with respect to the retrieval loops shown in FIG. 13 for both the cage and the insert. A variety of other features besides loops may be used to retrieve the components of the adjustable intra-atrial shunt. Thus, insert 35 is depicted with a snare leg 37 in FIG. 16 and with a "wind sock" or lengthened end 39 in FIG. 17. These features may also be added to the cage portions of the intra-atrial shunt for easy retrieval of the cage, and subsequent removal or re-positioning within the patient.

Figure 18:
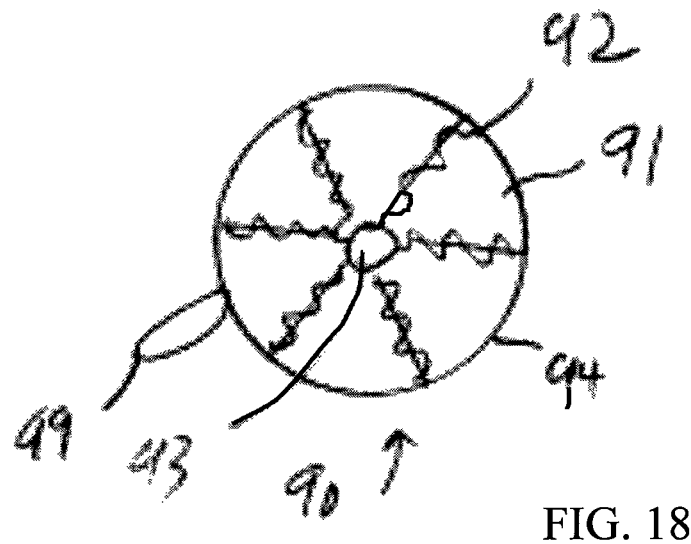
FIG. 18 is an end view of an insert portion of an embodiment of an implantable device.

The above embodiments are useful for adjusting the diameter of the shunt, but while useful, each adjustment is fixed. Other embodiments are constructed so that the openings or orifices gradually increase or decrease over time. In the embodiment of FIG. 18, flow control element or insert 90 has an outward form of a thin cylinder. Insert 90 includes a frame, which may include an outer circumference, and a plurality of flaps 91. The flaps are made of a polymer such as PTFE, UHMWPE, HDPE, polypropylene, polysulfone, or other biocompatible plastic. Other embodiments may use extracellular materials or other suitable biologic materials. The flaps are sewn together with biosorbable sutures, such as polylactic acid, polyglycolic acid and polycaprolactone, other suitable biosorbable sutures, or combinations of these. There may also be an initial orifice 93 in the center so that flow will occur upon placement of the insert 90 into a cage. The sutures provide tension between the flaps and keep the flaps closed. As the sutures absorb, the tension is lost and the flaps open. Other embodiments may include no initial orifice.

When insert 90 is first deployed, orifice 93 allows limited flow. Over time, material from the sutures will be absorbed gradually into the bloodstream. The sutures will become thinner and weaker, and the joint between any two of the flaps will become looser, allowing more blood flow. Some of the suture joints may use more sutures and some may use less, so that the weakening of the sutures increases gradually over time, rather than all at once. Accordingly, insert 90 will have an initially low flow of blood from an area of high pressure to low pressure, due to a small initial orifice. Later, as the sutures are biosorbed and the flap joints become looser, blood flow will increase. If more adjustment is needed, the insert 90 may be removed via retrieval loop 99 and replaced with another insert, such as one depicted in FIGS. 13-15 of the present application. Retrieval loop 99 is desirably not biosorbable and may include a radiopaque member as discussed above.

Figures 19A, 19B:
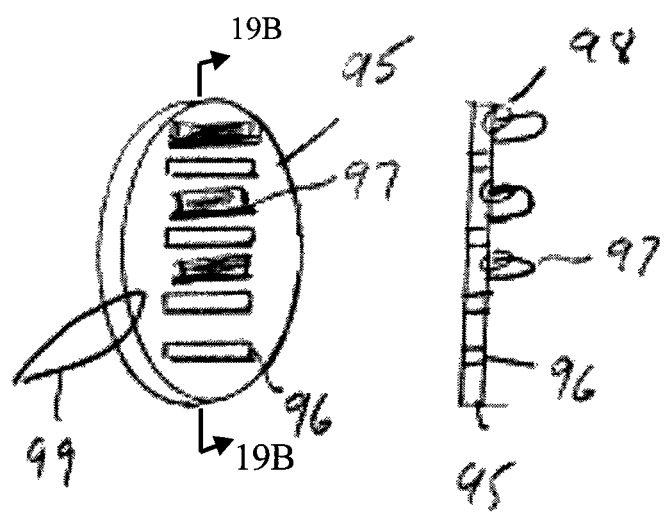
FIG. 19A is a perspective view of an insert portion of an embodiment of an implantable device.
FIG. 19B is a cross-sectional view taken along line 19B-19B of the insert portion of FIG. 19A.

The insert portion of another embodiment which utilizes an insert/cage combination is depicted in FIG. 19A. The insert portion of the inventive device of FIG. 19A is also shown in a cross-sectional view taken along line 19B-19B. In this embodiment, insert 95 may be a plate may of biocompatible plastic, with a plurality of orifices 96 and flaps 97 above the orifices, the flaps sewn in place as shown with biosorbable sutures. One or more of the orifices may have no flap, the orifice intended to provide an initial opening that remains constantly open while the insert 95 is deployed with a cage as shown above. When the insert is first deployed, the one or more orifices without flaps will provide flow. Over time, the sutures will be absorbed and will no longer be able to prevent the flaps 97 from covering the orifices, thus decreasing the openings and the flow from the area of high pressure to the area of low pressure. In some cases, the sutures provide tension to retain the flaps in place, keeping the flaps in place and the flaps open; as the sutures absorb, the flaps deploy to close the orifices. Insert 95 may be retrieved and removed via retrieval loop 99.

Figure 20:
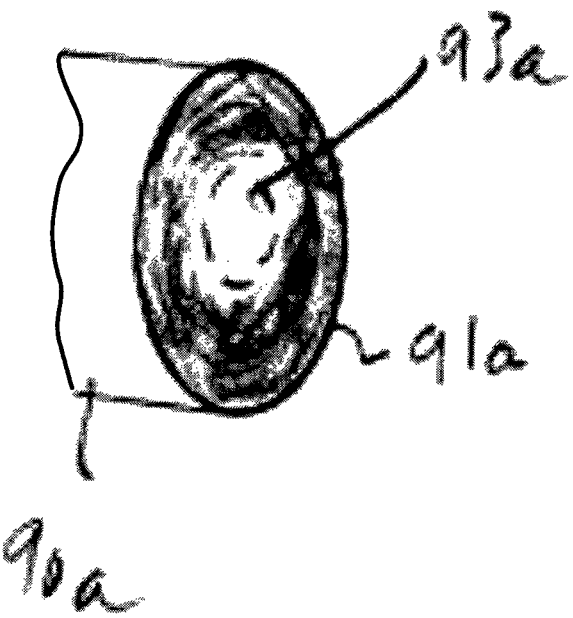
FIG. 20 is a partial perspective view of an end of an insert portion of an implantable device.
Figure 21:
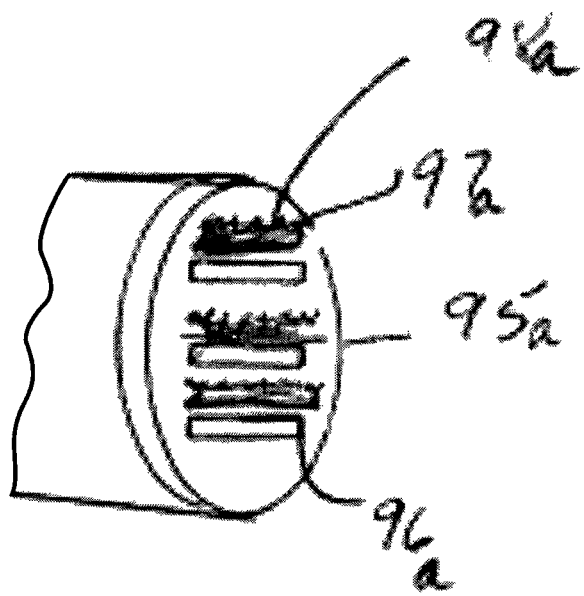
FIG. 21 is a partial perspective view of an end of an insert portion of an implantable device.

In some embodiments, the insert may be easier to fabricate if the flow control portions are placed near an end, i.e., an outside of the insert, as shown in FIGS. 20 and 21. For example, FIG. 20 depicts a tubular flow control element 90a, in the form of a hollow tube intended for placement within one of the retainers discussed above. In this example, a flow control element 91a is fabricated from a biosorbable polymer film, using biosorbable materials discussed above. The flow control element 91a may be fabricated with an initial orifice 93a, such as a central orifice, or it may be fabricated as a solid film, with no flow permitted through the device. Control of the absorption and loss of mass from the film may be easier to control with even a very small central orifice. After the flow control element in implanted into a patient, the film absorbs into the patient and becomes thinner and thinner, while the central orifice becomes larger and larger, allowing more blood flow as the orifice enlarges. In one embodiment, the thickness of the film may be graduated, with the thinnest portions at the center, with gradual thickening as the film approaches its circumference. The film may be bonded to the structure by ultrasonic bonding or other reliable method that prevents loosening or disassembly of the film from the structure during implantation. With this device, initial flow is low, but as the film absorbs into the patient, more and more flow is allowed as the orifice 93a grows.

Although the descriptions given above for the embodiments having inserts that the inserts were described as being removable, it is to be understood that the present invention also includes embodiments wherein the inserts are not removable. In some such embodiments, the inserts are permanently attached to the cage, and in still other embodiments what are described above as inserts are not inserts at all but are integral portions of the cage. It is also to be understood that in some embodiments, the first anchor, the second anchor, and the shunt are integrally connected.

In another embodiment, depicted in FIG. 21, a hollow flow control cylinder 95a includes one end with one or more orifices 96a. In this embodiment, one or more orifices, such as each orifice, is open and is near a flap 97a that is secured to the cylinder on one end. The other end of each flap is tethered to the cylinder with one or more biosorbable sutures 98a. Upon implantation, all the orifices will be open and will allow flow of blood. As the suture or sutures biosorb, the top end of each flap, as shown in FIG. 21, will become loose and may drop down to block the orifice 96a closest to that flap. Eventually, all the flaps will become loose and each flap will block the orifice closest to it, blocking flow of blood. However, the device of FIG. 21 may have one or more additional orifices without a flap, so that there is some blood flow even after all the sutures have absorbed. With this device, initial flow is relatively high, but as the sutures absorb into the patient, more and more of the orifices are blocked, cutting down flow, and if all orifices are blocked, flow is effectively stopped.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While embodiments have been disclosed and described in detail, it is understood that various modifications and improvements thereon will become readily apparent to those skilled in the art. Accordingly, the spirit and scope of the present invention is not limited by the foregoing examples, but is better understood by the claims below. All patents, published applications, and other documents identified herein are incorporated by reference herein in their entireties to the full extent permitted by law.

What is claimed is:

1. A device adapted for percutaneous delivery into a membrane of a patient's heart, the device comprising anchors which are adapted to hold the device in place within the aperture by contacting first and second sides of the membrane of the patient's heart, and a shunting section connected to the anchors, the shunting section having a first diameter at a first time after delivery and a second diameter at a second time after delivery, and the first time different from the second time, wherein the shunting section has a first length corresponding to the first diameter and a second length corresponding to the second diameter, the first length greater than the second length.

2. The device of claim 1, wherein the first diameter is less than the second diameter.

3. The device of claim 1, wherein the second diameter is less than the first diameter.

4. The device of claim 1, wherein at least a portion of the shunting section is biased to cause the shunting section to have a first hydraulic diameter.

5. The device of claim 4, wherein the shunting section is adapted to have a second hydraulic diameter upon removal of at least portion of the bias.

6. The device of claim 1, wherein at least one of the shunting section and the pair of anchors comprises a shape memory material.

7. The device of claim 1, wherein the shunting section is adapted to change from the first diameter to the second diameter automatically.

8. The device of claim 1, wherein the shunting section has a third diameter.

9. The device of claim 8, wherein the third diameter is greater than at least one of the first and second diameters.

10. The device of claim 8, wherein the third diameter is less than at least one of the first and second diameters.

11. The device of claim 8, wherein the shunting section is adapted to change from the second diameter to the third diameter automatically.

12. An expandable device adapted for percutaneous delivery into a membrane of a patient's heart, the device comprising:
    first and second anchors adapted to contact, respectively, a first side and a second side of the membrane of the patient's heart; and
    a shunt connected to the first and second anchors and having a bio-resorbable material, the shunt comprising a first inner diameter, changing to a second, different inner diameter, the second diameter greater than the first diameter;
    upon absorption of at least a portion of the bio-resorbable material.

13. The device of claim 12, wherein at least a portion of the shunting section is biased by the bio-resorbable material to cause the shunting section to have a first hydraulic diameter.

14. The device of claim 12, wherein the shunt is further adapted to permit blood to flow across the membrane at a third flow rate upon further absorption of at least a portion of the bio-resorbable material.

15. The device of claim 14, wherein the third flow rate is greater than at least one of the first and second flow rates.

16. The device of claim 14, wherein the third flow rate is less than at least one of the first and second flow rates.

17. The device of claim 12, further comprising a protruding member adapted to be engaged by a percutaneous retrieval device.

18. The device of claim 12, wherein each of the first and second anchors comprises a plurality of segments.

19. The device of claim 12, wherein the first anchor, the second anchor, and the shunt are integrally connected.

20. The device of claim 12, wherein the absorption of the bio-resorbable material occurs at a pre-determined rate.

21. An expandable device adapted for percutaneous delivery into a membrane of a patient's heart, the device comprising:
   first and second anchors adapted to contact, respectively, a first side and a second side of the membrane; and
   a shunt having a first dimension and connected to the first and second anchors, the shunt being adapted to permit blood to flow across the membrane at a first flow rate corresponding to a first dimension and comprising a frame having a plurality of struts,
   wherein at least a set of the struts are interconnected by a first bio-resorbable material configured to degrade while the struts remain,
   wherein the shunt has a first dimension when the first bio-resorbable material is intact and a second dimension when the first bio-resorbable material is not intact, and
   wherein the shunt is adapted to permit blood to flow across the membrane at a second flow rate corresponding to the second dimension.

22. The device of claim 21, wherein each of the first and second anchors comprises a plurality of segments.

23. The device of claim 21, wherein the first anchor, the second anchor, and the shunt are integrally connected.

24. The device of claim 21, wherein the absorption of the first bio-resorbable material occurs at a pre-determined rate.

25. The device of claim 21, further comprising a sheath situated within and attached to the frame.

26. The device of claim 21, wherein at least some of the struts are arranged in diamond-pattern sets, each of the diamond-pattern sets having a first and a second diagonal.

27. The device of claim 26, wherein at least some of the struts in the diamond-pattern sets are interconnected by the first bio-resorbable material to restrain the diamond-pattern sets to which the interconnected struts belong from changing the length of their respective first diagonals.

28. The device of claim 27, wherein the shunt has a longitudinal axis and at least some of the first diagonals are aligned parallel to the shunt's longitudinal axis.

29. The device of claim 27, further comprising a sheath situated within and attached to the frame.

30. The device of claim 21, wherein the shunt has a first end and a second end and at least one of the first and second ends is adapted to have a contracted configuration and a expanded configuration and the first bio-resorbable material interconnection is adapted to releasably maintain at least one of the first and second ends in at least one of its respective contracted and expanded configurations.

31. The device of claim 30, wherein the shunt further comprises a sheath situated within and attached to the frame.

32. The device of claim 21, wherein the shunt has a first end having a first contracted configuration and a first expanded configuration and a second end have a second contracted configuration and a second expanded configuration, the first end being constrained by the first bio-resorbable material to releasably maintain either its first expanded configuration or its first contracted configuration, and wherein the shunt has a second end having a second contracted configuration and a second expanded configuration, the second end being constrained by a second bio-resorbable material to releasably maintain either its second expanded configuration or its second contracted configuration, wherein the absorption of the first bio-esorbable material occurs at a first pre-determined rate and the absorption of the second bio-resorbable material occurs at a second pre-determined rate that is different than the first pre-determined rate.

33. The device of claim 32, wherein the shunt further comprises a sheath situated within and attached to the frame.

34. An expandable device adapted for percutaneous delivery into a membrane of a patient's heart, the device comprising:
   first and second anchors adapted to contact, respectively, a first side and a second side of the membrane;
   a core segment interconnecting the first and second anchors
   and comprising a bio-resorbable material, the core segment comprising a first diameter when the bio-resorbable material is intact, and a second, different diameter upon degradation of the bio-resorbable material, the second diameter greater than the first diameter.

35. The device of claim 34, wherein the shunt and the core segment are integrally connected.

* * * * *